(12) United States Patent
Cuevas Sànchez

(10) Patent No.: US 9,610,256 B2
(45) Date of Patent: Apr. 4, 2017

(54) METHODS OF USE FOR 2,5-DIHYDROXYBENZENE SULFONIC ACID COMPOUNDS FOR THE TREATMENT OF CANCER

(71) Applicant: AmDerma Pharmaceuticals, LLC, Bridgewater, NJ (US)

(72) Inventor: Pedro Cuevas Sànchez, Madrid (ES)

(73) Assignee: AmDerma Pharmaceuticals, LLC, Bridgewater, NJ (US)

( * ) Notice: Subject to any disclaimer, the term of this patent is extended or adjusted under 35 U.S.C. 154(b) by 0 days.

(21) Appl. No.: 14/933,422

(22) Filed: Nov. 5, 2015

(65) Prior Publication Data
US 2016/0058719 A1  Mar. 3, 2016

Related U.S. Application Data

(60) Continuation of application No. 14/537,972, filed on Nov. 11, 2014, now Pat. No. 9,301,931, which is a
(Continued)

(30) Foreign Application Priority Data

Feb. 17, 2004 (ES) .................................. 200400371

(51) Int. Cl.
*A61K 31/095* (2006.01)
*A61K 31/185* (2006.01)
(Continued)

(52) U.S. Cl.
CPC .......... *A61K 31/095* (2013.01); *A61K 31/185* (2013.01); *A61K 31/56* (2013.01);
(Continued)

(58) Field of Classification Search
None
See application file for complete search history.

(56) References Cited

U.S. PATENT DOCUMENTS

| 3,954,767 A | 5/1976 | Esteve-Subirana |
| 4,115,648 A | 9/1978 | Esteve-Subirana |

(Continued)

FOREIGN PATENT DOCUMENTS

| EP | 0204987 | 5/1986 |
| EP | 1719509 | 11/2006 |

(Continued)

OTHER PUBLICATIONS

Stockfleth et al. Successful treatment of actinic keratosis with imiquimod cream 5%: a report of six cases. British Journal of Dermatology, 2001; 144: 1050-1053.*
(Continued)

*Primary Examiner* — Anna Pagonakis
(74) *Attorney, Agent, or Firm* — Servilla Whitney LLC

(57) ABSTRACT

The invention describes compositions and methods of use for 2,5-dihydroxybenzene sulfonic acid compounds and pharmaceutically acceptable salts thereof. The invention provides methods for (a) treating skin cancer; (b) treating cancer of the organs; (c) treating leukemia; (d) improving the efficacy of chemotherapy, radiation therapy and/or cancer immunotherapy; (e) treating rosacea; and (f) treating psoriasis by administration of a composition comprising at least one 2,5-dihydroxybenzene sulfonic acid compound or a pharmaceutically acceptable salt thereof, and, optionally at least one therapeutic agent. Also disclosed are compositions comprising administration of at least one 2,5-dihydroxybenzene sulfonic acid compound, or a pharmaceutically acceptable salt thereof, and, at least one therapeutic agent. In the invention the 2,5-dihydroxybenzene sulfonic acid compounds or pharmaceutically acceptable salts thereof are
(Continued)

2,5-dihydroxybenzene sulfonic acid, calcium 2,5-dihydroxybenzenesulfonate, potassium 2,5-dihydroxybenzenesulfonate, magnesium 2,5-dihydroxybenzenesulfonate and diethylamine 2,5-dihydroxybenzenesulfonate.

6 Claims, 18 Drawing Sheets

Related U.S. Application Data continuation of application No. 13/937,464, filed on Jul. 9, 2013, now Pat. No. 8,912,171, which is a division of application No. 12/257,854, filed on Oct. 24, 2008, now Pat. No. 8,497,257, which is a division of application No. 11/506,469, filed on Aug. 16, 2006, now abandoned, which is a continuation-in-part of application No. 10/588,166, filed as application No. PCT/ES2005/070017 on Feb. 16, 2005, now Pat. No. 7,968,531.

(51) Int. Cl.
| | | |
|---|---|---|
| A61K 31/56 | (2006.01) | |
| A61K 31/59 | (2006.01) | |
| A61K 31/60 | (2006.01) | |
| A61K 45/06 | (2006.01) | |
| C07C 309/29 | (2006.01) | |

(52) U.S. Cl.
CPC .............. *A61K 31/59* (2013.01); *A61K 31/60* (2013.01); *A61K 45/06* (2013.01); *C07C 309/29* (2013.01)

(56) References Cited

U.S. PATENT DOCUMENTS

| | | | |
|---|---|---|---|
| 4,654,323 | A | 3/1987 | Beitner et al. |
| 4,837,378 | A | 6/1989 | Borgman |
| 4,970,202 | A | 11/1990 | Trigger |
| 5,374,772 | A | 12/1994 | Carson et al. |
| 5,519,018 | A | 5/1996 | Matusch et al. |
| 5,656,286 | A | 8/1997 | Miranda et al. |
| 5,698,595 | A | 12/1997 | Boelle et al. |
| 6,281,203 | B1 | 8/2001 | Touzan et al. |
| 6,664,406 | B1 | 12/2003 | Coupland et al. |
| 6,787,573 | B2 | 9/2004 | Nottet |
| 6,866,678 | B2 | 3/2005 | Shenderova et al. |
| 7,968,531 | B2 | 6/2011 | Cuevas Sanchez et al. |
| 8,435,971 | B2 | 5/2013 | Cuevas Sanchez et al. |
| 8,436,045 | B2 | 5/2013 | Cuevas Sanchez |
| 8,497,257 | B2 | 7/2013 | Cuevas Sanchez |
| 2002/0143052 | A1 | 10/2002 | Lan-Hargest et al. |
| 2003/0216418 | A1 | 11/2003 | Stogniew et al. |
| 2004/0167222 | A1 | 8/2004 | Brooks et al. |
| 2005/0175559 | A1 | 8/2005 | DiNardo et al. |
| 2006/0258730 | A1 | 11/2006 | Allegretti et al. |
| 2007/0032471 | A1 | 2/2007 | Torrens Jover et al. |
| 2007/0149618 | A1 | 6/2007 | Cuevas Sanchez et al. |
| 2008/0113947 | A1 | 5/2008 | Cuevas Sanchez et al. |
| 2008/0113948 | A1 | 5/2008 | Cuevas Sanchez et al. |
| 2008/0114060 | A1 | 5/2008 | Cuevas Sanchez et al. |
| 2008/0114063 | A1 | 5/2008 | Sanchez et al. |
| 2008/0114075 | A1 | 5/2008 | Cuevas Sanchez et al. |
| 2008/0125485 | A1 | 5/2008 | Cuevas Sanchez et al. |
| 2008/0125486 | A1 | 5/2008 | Sanchez et al. |
| 2008/0226571 | A1 | 9/2008 | Majeed |
| 2009/0111779 | A1 | 4/2009 | Cuevas Sanchez et al. |
| 2013/0202580 | A1 | 8/2013 | Cuevas Sanchez et al. |
| 2013/0203851 | A1 | 8/2013 | Cuevas Sanchez et al. |
| 2015/0141476 | A1 | 5/2015 | Cuevas Sanchez et al. |

FOREIGN PATENT DOCUMENTS

| | | | |
|---|---|---|---|
| JP | 82-83152 | | 10/1996 |
| WO | WO-96/17589 | | 6/1996 |
| WO | WO-96/25159 | | 8/1996 |
| WO | WO-2005/013962 | | 2/2005 |
| WO | WO-2005/023305 | | 3/2005 |
| WO | WO 2005/077352 | * | 8/2005 |
| WO | WO-2005/077352 | | 8/2005 |
| WO | WO-2006/029484 | | 3/2006 |
| WO | WO-2006/069806 | | 7/2006 |

OTHER PUBLICATIONS

Cuevas. J. Am. Acad. Dermatol., Sep. 2005, vol. 53, No. 3, pp. 526-527.*
*International Journal of Clinical Practice*, vol. 53 No. 8 Dec. 1999, 8 pgs.
Actinic Keratosis and Other Precancers, http//www.skincancer.org 2008, 3 pgs.
Catalogo de especialidades farmaceuticas 1991, *Consejo General De Colegios Oficiales De Farmaceuticos* 1991, 4 pgs.
Causes of Barrett's Esophagus, http://digestive-system.emedtv.com/barrett's-esophagus/causes-of-barrett's-esophagus.html Nov. 2006, 3 pgs.
Crohn's Disease, http://cholitis.emedtv.com/crohn'sdisease/crohn's-disease-causes.html 2008, 3 pgs.
Definition of Rosacea, *American Heritage Medical Dictionary*, www.freedictionary.com 2007, 6 pgs.
English translation of Acnisdin and Acnisdin Retinoico entries in Catalogo de especialidades farmaceuticas, *Consejo General de Colegios Oficiales De Farmaceuticos* 1991, 2 pages.
Final Office Action in U.S. Appl. No. 12/257,854, dated Mar. 1, 2012, 9 pages.
Final Office Action in U.S. Appl. No. 12/946,742, mailed Jun. 15, 2012, 11 pages.
Final Office Action in U.S. Appl. No. 13/767,122, dated Jun. 27, 2014, 18 pages.
Final Office Action in U.S. Appl. No. 13/772,790, dated Apr. 22, 2014, 11 pages.
Final Office Action in U.S. Appl. No. 13/772,790, dated Sep. 24, 2014, 13 pages.
Final Office Action in U.S. Appl. No. 13/937,464, dated Jul. 29, 2014, 8 pages.
Final Office Action in U.S. Appl. No. 11/506,469, dated Nov. 24, 2008, 14 pages.
Final Office Action in U.S. Appl. No. 14/537,972, dated Oct. 29, 2015, 9 pages.
Glioma Brain Tumors, http://www.sfn.org/index.aspx?pagename=brainbriefings_gliomabraintumors 2008, 2 pages.
International Search Report of PCT/EP2007/058438, mailed on Nov. 27, 2007, 4 pages.
International Search Report of PCT/EP2007/058439, mailed on Nov. 28, 2007, 4 pages.
International Search Report of PCT/EP2007/058440, mailed on Feb. 22, 2008, 5 pages.
International Search Report of PCT/EP2007/058441, mailed on Nov. 14, 2007, 4 pages.
International Search Report of PCT/EP2007/058443, mailed on Nov. 9, 2007, 3 pages.
International Search Report of PCT/EP2007/058444, mailed on Nov. 28, 2007, 4 pages.
International Search Report of PCT/EP2007/058445, mailed on Nov. 26, 2007, 4 pages.
International Search Report of PCT/EP2007/058446, mailed on Nov. 30, 2007, 4 pages.
International Search Report of PCT/EP2007/058447, mailed on Dec. 3, 2007, 4 pages.
International Search Report of PCT/EP2007/058451, mailed on Nov. 30, 2007, 4 pages.
International Search Report of PCT/EP2007/058453, mailed on Jul. 15, 2008, 6 pages.

(56) References Cited

OTHER PUBLICATIONS

International Search Report of PCT/EP2007/058454, mailed on Feb. 19, 2008, 4 pages.
International Search Report of PCT/EP2007/058456, mailed on Dec. 6, 2007, 7 pages.
International Search Report of PCT/ES2005/070017, mailed on Jun. 22, 2005, 2 pages.
Non-Final Office Action in U.S. Appl. No. 12/257,854, dated Oct. 26, 2011, 7 pages.
Non-Final Office Action in U.S. Appl. No. 12/946,742, dated Dec. 30, 2011, 8 pages.
Non-Final Office Action in U.S. Appl. No. 13/169,781, dated Sep. 14, 2012, 17 pages.
Non-Final Office Action in U.S. Appl. No. 13/767,122, dated Jan. 16, 2014, 27 pages.
Non-Final Office Action in U.S. Appl. No. 13/1767,122, dated Sep. 8, 2014, 14 pages.
Non-Final Office Action in U.S. Appl. No. 13/772,790, dated Jul. 18, 2014, 13 pages.
Non-Final Office Action in U.S. Appl. No. 13/772,790, dated Jan. 2, 2014, 3 pages.
Non-Final Office Action in U.S. Appl. No. 13/937,464, dated Apr. 23, 2014, 21 pages.
Non-Final Office Action in U.S. Appl. No. 10/588,166, dated Dec. 30, 2009, 10 pages.
Non-Final Office Action in U.S. Appl. No. 11/506,469, dated Mar. 16, 2011, 5 pages.
Non-Final Office Action in U.S. Appl. No. 11/506,469, dated Jun. 3, 2008, 18 pages.
Non-Final Office Action in U.S. Appl. No. 14/537,972, dated Aug. 17, 2015, 9 pages.
PCT IPRP in PCT/EP2007/058438, dated Nov. 21, 2008, 8 pages.
PCT IPRP in PCT/EP2007/058439, dated Dec. 1, 2008, 6 pages.
Psoriasis—Basics Facts—What Is Psoriasis, http://www.psoriasisguide.com/usus_basics/what_is_psoriasis.html 2005, 2 pages.
Reply to Written Opinion in PCT/EP2007/058440, dated Jul. 17, 2008, 30 pages.
Structure-Activity Relationship and Drug Design, *Remington's Pharmaceutical Sciences* (Sixteenth Edition) 1980, 7 pages.
WrinkleReducer 101: Preventing and Treating Skin Wrinkles, http://wrinklereducer101/com/skin-wrinkles.php retrieved Aug. 10, 2010, 3 pages.
Written Opinion of PCT/EP2007/058438, mailed Nov. 27, 2007, 7 pages.
Written Opinion of PCT/EP2007/058440, mailed Feb. 22, 2008, 8 pages.
Written Opinion of PCT/ES2005/070017, mailed on Jun. 22, 2005, 3 pages.
Adank, Christian, et al., Calcium Dobesilate in Diabetic Retinopathy, *Ophthalmologica*, Basel 190 1985, 102-111.
Angulo, Javier, et al., Calcium dobesilate potentiates endothelium-derived hyperpolarizing factor-mediated relaxation of human penile resistance arteries, *British Journal of Pharmacology* 2003, 1-9.
Anwar, Jamshaid, et al., The Development of Actinic Keratosis into Invasive Squamous Cell Cardinoma: Evidence and Evolving Classification Schemes, *Clinics in Dermatology* 22 2004, 189-196.
Arhanic, V., et al., Attempts at Treating Bureosis with Angioprotective Agents, *Annals of the Dr. M. Stojanovic Hospital*, vol. 15:120 1976, 9 pages.
Banarroch, Isaac S., et al., Treatment of Blook Hyperviscosity with Calcium Dobesilate in Patients with Diabetic Retinopathy, *Ophthalmic Res.* 17 1985, 131-138.
Bello, A. A., et al., Calcium Dobesilate Combined With a Heparinoid in the Topical Treatment of Chronic Venous Insufficiency: A Doubleblind Study, *Acta Therapeutica* vol. 16 1990, 79-86.
Benakis, A., et al., Localisation, distribution, eliination et metabolisme du dihydroxy-2,5, benzene sulfonate de Ca (Dobesilate de Ca) marque par le S35 chez la souris, le rat et le lapin, *Congres International de Therapeutique* 1974, 16 pages.
Berge, Stephen M., et al., Pharmaceutical Salts, *Journal of Pharmaceutical Sciences*, vol. 66 No. 1 Jan. 1977, 1-19.
Berthet, P., et al., Calcium Dobesilate: Pharmacological Profile Related to its Use in Diabetic Retinopathy, *IJCP*, vol. 53, No. 8 Dec. 1999, 631-636.
Bhushan, M., et al., Recent advances in cutaneous angiogenesis, *British Journal of Dermatology* 147 2002, 418-425.
Brannon, MD, Heather, Atopic Dermatitis Treatment, http://dermatology.about.com/cs/eczemadermatitis/a/stopictx.htm Dec. 23, 2005, 2 pages.
Brunet, J., et al., In vitro antioxidant properties of calcium dobesilate, *Fundam. Clin. Pharmacol.* 12 1998, 205-212.
Buyuk, Arzu, et al., Oral Metronidazole treatment of lichen planus, *J. Am. Acad. Dermatol*. vol. 43 No. 2 Part 1, 2000, 260-262.
Cohen, et al., Diagnosis and Treatment of Rosacea *J. Am. Board. Fam. Pract*. vol. 15 214-217.
Cuevas, Pedro, et al., Dobesilate in the Treatment of Plaque Psoriasis, *Eur. J. Med. Res. 10* 2005, 373-376.
Cuevas, P., et al., Therapeutic Response of Rosacea to Dobesilate, *Eur. J. Med. Res.*, vol. 10 2005, 454-456.
Cuevas, P., et al., Topical Treatment of Actinic Keratoses with Potassium Dobesilate 5% Crams. A Preliminary Open-Label Study, *Eur. J. Med Res* 16 2011, 67-70.
Cuevas, P., et al., Treatment of basal cell carcinoma with dobesilate, *Am. Acad. Dermatol*. 2005, 526-527.
Divers, A.K., et al., Keratoacanthoma centrifugum marginatum: a diagnostic and therapeutic challenge, *Curtis*, vol. 73, No. 4 2004, 257-262.
Dormond, Olivier, et al., Inhibitor of tumor angiogenesis by non-steroidal anti-inflammatory drugs: emerging mechanisms and therapeutic perspectives, *Drug Resistance Updates 4* 2002, 314-321.
Dorwald, F. Z., Side Reactions in Organic Synthesis. A Guide to Successful Synthesis Design, *Wiley-VCH Verlag GmbH & Co*. 2005, 4 pages.
Fimmel, Sabine et al., New aspects of the pathogenesis of rosacea, *Drug Discovery Today: Disease Mechanisms*, vol. 5 No. 1 2008, 103-111.
Gambichler, T., et al., Cytokine mRNA expression in basal cell carcinoma, *Arch Dermatol Res 298* 2006, 139-141.
Goldman, Lee, et al., Principles of Cancer Therapy, *Cecil Textbook of Medicine*, vol. 1, W.B. Saunders Company 2000, 1060-1074.
Graber, R., et al., Calcium Dobesilate protects human peripheral blood mononuclear cells from oxidation and apoptosis, *Apoptosis 3* 1998, 41-49.
Hodge, David R., et al., The role of IL-6 and STAT3 in inflammation and cancer, *European Journal of Cancer 41* 2005, 2502-2512.
Hornick, Jason L., et al., A New Chemically Modified Chimeric TNT-3 Monoclonal Antibody Directed Against DNA for the Radioimmunotherapy of Solid Tumors, *Cancer Biotherapy & Radiopharmaceuticals*, vol. 13, No. 4 1998, 255-268.
Jee, Shiou-Hwa, et al., Interleukin-6 Induced Basic Fibroblast Growth Factor-Dependent Angiogenesis in Basal Cell Carcinoma Cell Line via JAK/STAT3 and PI3-Kinase/Akt Pathways, *J Invest Dermatology 123* 2004, 1169-1175.
Jee, Shiou-Hwa, et al., Overexpression of interleukin-6 in human basal cell carcinoma cell lines increases anti-apoptotic activity and tumorigenic potency, *Onogena 20* 2001, 198-208.
Jee, S. H., et al., The Phosphotidyl Inositol 3-Kinase/Akt Signal Pathway is Involved in Interleukin-6-mediated Mcl-1 Upregulation and Anti-apoptosis Activity in Vasal Cell Carcinoma Cells, *The Journal of Investigative Dermatology*, vol. 119, No. 5 2002, 1121-1127.
Jegasothy, Brian V., et al., Tacrolimus (FK 506)—A New Therapeutic Agent for Severe Recalcitrant Psoriasis, *Arch Dermatol*, vol. 128 Jun. 1992, 781-785.
Johnson, JL, et al., *British Journal of Cancer* 84(10) 2001, 1424-1431.
Jordan, V. C., Tamoxifen: A Most Unlikely Pioneering Medicine, *Nature Reviews Drug Discovery*, vol. 2 2003, 205-213.
Karasek, Marvin A., Progress in our understanding of the biology of psoriasis, *Cutis*, vol. 64, Issue 5 Nov. 1999, 5 pages.

(56) References Cited

OTHER PUBLICATIONS

Kaur, Charandeep, et al., An open trial of calcium dobesilate in patients with venous ulcers and stasis dermatitis, *International Journal of Dermatology 42* 2003, 147-152.
Khawli, Leslie A., et al., Comparison of Recombinant Derivatives of Chimeric TNT-3 Antibody for the Radioimaging of Solid Tumors, *Hybridoma and Hybridomics*, vol. 22, No. 1 2003, 1-10.
Kocak, MD, Mukadder, et al., Examination of Bcl-2, Bcl-X and bax protein expression in psoriasis, *International Journal of Dermatology 42* 2003, 789-793.
Lameynardie, Stephane, et al., Inhibition of choroidal angiogenesis by calcium dobesilate in normal Wistar and disbetic GK rats, *European Journal of Pharmacology 510* 2005, 149-156.
Lens, M., et al., Current clinical overview of cutaneous melanoma, *British Journal of Nursing*, vol. 17, No. 5 2008, 2 pages.
Losa, Gabriele A, et al., Prevention of Oxidation and Apoptosis in Human Peripheral Blood Mononuclear Cells Exposed to Caldium Dobesilate, *International Journal of Angiology 8* 1999, 511-515.
Lozano, Rosa M., et al., Solution Structure of Acidic Fibroblast Growth Factor Bound to 1,3,6-Naphthalenetrisulfonate: A Minimal Model for the Anti-tumoral Actionof Suramins and Suradistas, *J. Mol. Biol. 281* 1998, 899-15.
Maddin, Stuart, A comparison of topical azelaic acid 20% cream and topical metronidazole 0.75% cream in the treatment of patients with papulopustular rosacea, *Journal of the American Academy of Dermatology*, vol. 40 No. 6, Part 1, Jun. 1999, 5 pages.
Michal, M., et al., Effect of Calcium Dobesilate on Platelet Function, *Thrombosis Research 51* 1988, 593-605.
Nestor, Mark S., et al., The Use of Photodynamic Therapy in Dermatology: Results of a Consensus Conference, *Journal of Drugs in Dermatology*, vol. 5 Issue 2 Feb. 2006, 140-154.
Newell, B., et al., Comparison of the microvasculature of basal cell carcinoma and actinic keratosis using intravital microscopy and immunohistochemistry, *British Journal of Dermatology 149* 2003, 105-110.
Niwa, Y., et al., Topical application of the immunosuppressant tacrolimus accelerates carcinogenesis in mouse skin, *British Journal of Dermatology 149* 2003, 960-67.
Nour, A. F., et al., Preliminary Clinical Study with Calcium Dobesilate in Fibrocystic Disease of the Breast, *Acta Therapeutica*, vol. 12. No. 3 1986, 233-241.
O'Grady, Anthony, et al., COX-2 Expression Correlates With Microvessel Density in Non-Melanoma Skin Cancer From Renal Transplant Recipients and Immunocompetent Individuals, *Human Pathology*, vol. 35, No. 12 2004, 1549-1555.
Oh, Chang-Keun, et al., Expression of Basic Fibroblast Growth Factor, Vascular Endothelial Growth Factor, and Thrombospondin-1 Related to Microvessel Density in Nonaggressive and Aggressive Basal Cell Carcinomas, *The Journal of Dermatology*, Vo. 30 2003, 306-313.
Peck, M.D., Gary, L. , Topical tretinoin in actinic Keratosis and basal cell carcinoma, *Journal of the American Academy of Dermatology*, vol. 15, Issue 4, Part 2 (Abstract Only) Oct. 1986 , 2 pgs.
Pelle, Michelle, T., et al., Rosacea: II. Therapy, *J Am Acad Dematol*, vol. 51 2004, 499-512.
Rhodes, Christopher T., Modern Pharmaceutics, 3rd Edition, Revised and Expanded, *Marcel Dekker, Inc*., 3 pages.
Ruiz, Emilio, et al., Calcium Dobesilate Increases Endothelium-Dependent Relaxation in Endothelium-Injured Rabbit Aorta, *Pharmacological Research*, vol. 38, No. 5 1998, 361-366.
Rutkowski, Suzanne, Mystified by Your Medications?, *Asthma Magazine* 2001, 9-12.
Sausville, Edward, A., et al., Contributions of Human Tumor Xenografts to Anticancer Drug Development, *Cancer Res 66*(7) Apr. 1, 2006, 3351-3354.
Schon, MD, Michael, et al., Psoriasis, *The New England Journal of Medicine* 2005, 1899-1912.
Schulze, H. J., et al., Imiquimod 5% cream for the treatment of superficial basal cell carcinoma: results from a randomized vehicle-controlled phase III study in Europe, *British Journal of Dermatology 152* 2005, 939-947.
Sintov, Amnon C., et al., Percutaneous penetration and skin metabolism of ethylsalicylate-containing agent, UT-2100: in-vitro and in-vivo evaluation in guinea pigs, *Journal of Controlled Release 79* 2002, 113-122.
Skov, L., et al., Basal cell carcinoma is associated with high TNF-a release but not with TNF-a polymorphism at position 308, *Experimental Dermatology 12* 2003, 772-776.
Staibano, MD, S., et al., The Prognostic Significance of Tumor Angiogenesis in Nonaggressive and Aggressive Basal Cell Carcinoma of the Human Skin, *Human Pathology*, vol. 27 No. 7 1996, 695-700.
Stanton, Anthony W., et al., Expansion of Micorvascular Bed and Increased Solute Flux in Human Basal Cell Carcinoma in Vivo, Measured by Fluorescein Video Angiography, *Cancer Research 63* 2003, 3969-3979.
Stanwell, Caroline, et al., The Erbstatin Analogue Methyl 2,5-Dihydroxycinnamate Cross-Links Proteins and is Cytotoxic to Normal and Neoplastic Epithelial Cells by a Mechanism Independent of Tyrosine Kinase Inhibition, *Cancer Research*, vol. 55 1995, 4950-4956.
Stockfleth, E., et al., Successful treatment of actinic keratosis with imiquimod cream 5%: a report of six cases, *British Journal of Dermatology*, 144 2001, 1050-1053.
Suschek, Christoph, et al., Dobesilate enhances endothelial nitric oxide synthase-activity in macro-and microvascular endothelial cells, *British Journal of Pharmacology 122* 1997, 1502-1508.
Takatsuka, Yoshikazu, et al., Various Analogues to Anthranilic Acid and Their Anti-Cancer Effects, *Mie Medical Journal*, vol. XVII, No. 1 1987, 11 pages.
Tejerina, T., et al., Calcium Dobesilate: Pharmacology and Future Approaches, *Gen. Pharmac*. vol. 31, No. 3 1998, 357-360.
Tejerina, Teresa, et al., Calcium Dobesilate Attenuates the Vascular Injury and the Progression of Diabetic Retinopathy in Diabetic Rats (STZ) *FASEB Journal*, vol. 15 No. 4 2001, A 215.
Tjiu, Jeng-Wei , et al., Cyclooxygenase-2 Overexpression in Human Basal Cell Carcinoma Cell Line Increases Antiapoptosis, Angiogenesis, and Tumorigenesis, *The Society for Investigative Dermatology* 2006, 1143-1151.
Tjiu, Jeng-Wei, et al., Tumor-Associated macrophage-Induced Invasion and Angiogenesis of Human Basal Cell Carcinoma Cells by Cyclooxygenase-2 Induction, *Journal of Investigative Dermatology* 2009, 1016-1025.
Travis, Lisa , et al., Medical Backgrounder: Psoriasis, *Drugs of Today*, 38 (12) 2002, 847-865.
Trozak, Daniel J., Topical corticosteriod therapy in psoriasis vulgaris: Update and new strategies, *Cutis*, vol. 64, Iss. 5 Nov. 1999, 5 pages.
Vippagunta, Sudha R., et al., Crystalline solids, *Advanced Drug Delivery Reviews 48* 2001, 3-26.
Wilkin, Jonathan, et al., Standard classification of rosacea: Report of the National Rosacea Society Expert Committee on the Classification and Staging of Rosacea, *Acad. Derato. 46:L* 2002 , 584-587.
Wolff, Manfred, E., Burger's medicinal Chemistry and Drug Discovery, Fifth Edition vol. 1: *Principles and Practice* 1995, 4 pages.
Wollina, U., et al., Toxicity of Methotrexate Treatment in Psoriasis and Psoriatic Arthritis—Short and Long-Germ Toxicity in 104 Patients, *Clin Rheumatol 20* 2001, 406-410.
Yamada, Katsuhisa, et al., Inhibitory Effect of Diacetyl Gentisic Acid on Melanogenesis, *Journal of Japanese Cosmetic Science Society*, vol. 22, 1998, 169-174.

* cited by examiner

METHODS OF USE FOR 2,5-DIHYDROXYBENZENE SULFONIC ACID COMPOUNDS FOR THE TREATMENT OF CANCER

CROSS-REFERENCE TO RELATED APPLICATIONS

This application is a continuation of U.S. application Ser. No. 14/537,972, filed Nov. 11, 2014, which is a continuation of U.S. application Ser. No. 13/937,464, filed Jul. 9, 2013 and issued as U.S. Pat. No. 8,912,171 on Dec. 16, 2014, which is a divisional of U.S. application Ser. No. 12/257,854, filed Oct. 24, 2008 and issued as U.S. Pat. No. 8,497,257 on Jul. 30, 2013, which is a divisional of U.S. application Ser. No. 11/506,469, filed Aug. 16, 2006 and now abandoned, which is a continuation-in-part of U.S. application Ser. No. 10/588,166 and issued as U.S. Pat. No. 7,968,531 on Jun. 28, 2011, which is the 35 U.S.C. §371 National Stage application of International Application PCT/ES2005/070017, filed Feb. 16, 2005, which claims the benefit of priority of Spanish Application No. P200400371, filed Feb. 17, 2004. The foregoing applications, and all documents cited therein, are incorporated herein by reference in their entirety.

FIELD OF THE INVENTION

The invention describes compositions and methods of use for 2,5-dihydroxybenzene sulfonic acid compounds and pharmaceutically acceptable salts thereof. The invention provides methods for (a) treating skin cancer; (b) treating cancer of the organs; (c) treating leukemia; (d) improving the efficacy of chemotherapy, radiation therapy and/or cancer immunotherapy; (e) treating rosacea; and (f) treating psoriasis by administration of a composition comprising at least one 2,5-dihydroxybenzene sulfonic acid compound or a pharmaceutically acceptable salt thereof, and, optionally at least one therapeutic agent. Also disclosed are compositions comprising administration of at least one 2,5-dihydroxybenzene sulfonic acid compound, or a pharmaceutically acceptable salt thereof, and, at least one therapeutic agent. In the invention the 2,5-dihydroxybenzene sulfonic acid compounds or pharmaceutically acceptable salts thereof are 2,5-dihydroxybenzene sulfonic acid, calcium 2,5-dihydroxybenzenesulfonate, potassium 2,5-dihydroxybenzenesulfonate, magnesium 2,5-dihydroxybenzenesulfonate and diethylamine 2,5-dihydroxybenzenesulfonate.

BACKGROUND OF THE INVENTION

Despite recent advances in chemotherapy and radiation, cancer is one of the leading causes of death at any age in the United States. There are nearly three million new cancer cases diagnosed every year. The overall five-year survival approximates fifty percent for all patients, and the prognosis remains particularly poor for those with advanced solid tumors.

Rosacea is a common facial and eye disease that currently affects millions worldwide. It is a chronic and progressive cutaneous vascular disorder, primarily involving the malar and nasal areas of the face. Rosacea is characterized by flushing, erythema, papules, pustules, telanglectasia, facial edema, ocular lesions, and, in its most advanced and severe form, hyperplasia of tissue and sebaceous glands leading to rhinophyma. Rhinophyma, a florid overgrowth of the tip of the nose with hypervascularity and modularity, is an unusual progression of rosacea of unknown cause. Ocular lesions are common, including mild conjunctivitis, burning, and grittiness. Blepharitis, the most common ocular manifestation, is a nonulcerative condition of the lid margins.

Psoriasis is a chronic disease that affects about 2-3% of the world population. It is characterized by hyperproliferation of epidermal cells. The symptoms of psoriasis include sharply defined erythematous patches covered with a distinctive scale, hyperproliferation of the epidermis, incomplete differentiation of keratinocytes and dermal inflammation. Clinical variants of psoriasis include erythroderma, seborrheic, inverse, guttate, and photosensitive psoriasis, pustular variants and Reiter's disease. Currently there is no cure for psoriasis There is still a need in the art for new effective therapies to treat cancer, to treat rosacea and to treat psoriasis. The invention is directed to these, as well as other, important ends.

SUMMARY OF THE INVENTION

The invention describes methods for (a) treating skin cancer; (b) treating cancer of an organ; (c) treating leukemia; and (d) improving the efficacy of chemotherapy, radiation therapy and/or cancer immunotherapy in a patient in need thereof comprising administering to the patient an effective amount of at least one 2,5-dihydroxybenzene sulfonic acid compound or a pharmaceutically acceptable salt thereof. The methods can optionally further comprise the administration of at least one therapeutic agent, such as, for example, chemotherapeutic agents, steroids, retinoids, antimicrobial compounds, antioxidants, anti-inflammatory compounds, NMDA receptor antagonists, endothelin antagonists, immunomodulating agents, vitamin D analogues, salicylic acid, and combinations of two or more thereof. In this embodiment of the invention, the methods can involve (i) administering the 2,5-dihydroxybenzene sulfonic acid compound, or (ii) administering the 2,5-dihydroxybenzene sulfonic acid compound and at least one therapeutic agent. The 2,5-dihydroxybenzene sulfonic acid compounds and/or therapeutic agents can be administered separately or as components of the same composition in one or more pharmaceutically acceptable carriers.

The invention describes methods for treating rosacea in a patient in need thereof comprising topically administering to the patient an effective amount of at least one 2,5-dihydroxybenzene sulfonic acid compound or a pharmaceutically acceptable salt thereof. The methods can optionally further comprise the administration of at least one therapeutic agent, such as, for example, chemotherapeutic compounds, NMDA receptor antagonists, endothelin antagonists, immunomodulating agents, vitamin D analogues, salicylic acid, and combinations of two or more thereof. In the embodiment of the invention, the methods can involve (i) topically administering the 2,5-dihydroxybenzene sulfonic acid compound, or (ii) topically administering the 2,5-dihydroxybenzene sulfonic acid compound and at least one therapeutic agent. The 2,5-dihydroxybenzene sulfonic acid and/or therapeutic agents can be administered separately or as components of the same composition in one or more pharmaceutically acceptable carriers.

The invention describes methods for treating psoriasis in a patient in need thereof comprising topically administering to the patient an effective amount of at least one 2,5-dihydroxybenzene sulfonic acid compound or a pharmaceutically acceptable salt thereof. The methods can optionally further comprise the administration of at least one therapeutic agent, such as, for example, chemotherapeutic agents, steroids, retinoids, antimicrobial compounds, antioxidants, anti-inflammatory compounds, NMDA receptor antagonists, endothelin antagonists, immunomodulating agents, vitamin D analogues, salicylic acid, and combinations of two or more thereof. In this embodiment of the invention, the methods can involve (i) topically administering the 2,5-dihydroxybenzene sulfonic acid compound, or (ii) topically administering the 2,5-dihydroxybenzene sulfonic acid compound and at least one therapeutic agent. The 2,5-dihydroxybenzene sulfonic acid and/or therapeutic agents can be administered separately or as components of the same compositions in one or more pharmaceutically acceptable carriers.

The invention provides compositions comprising at least one 2,5-dihydroxybenzene sulfonic acid compound and at least one therapeutic agent, including, but not limited to, chemotherapeutic agents, steroids, retinoids, antimicrobial compounds, antioxidants, anti-inflammatory compounds, NMDA receptor antagonists, endothelin antagonists, immunomodulating agents, vitamin D analogues, salicylic acid, and combinations of two or more thereof. The invention also provides for such compositions in a pharmaceutically acceptable carrier.

These and other aspects of the present invention are explained in detail herein.

DETAILED DESCRIPTION OF THE INVENTION

Figure 1:
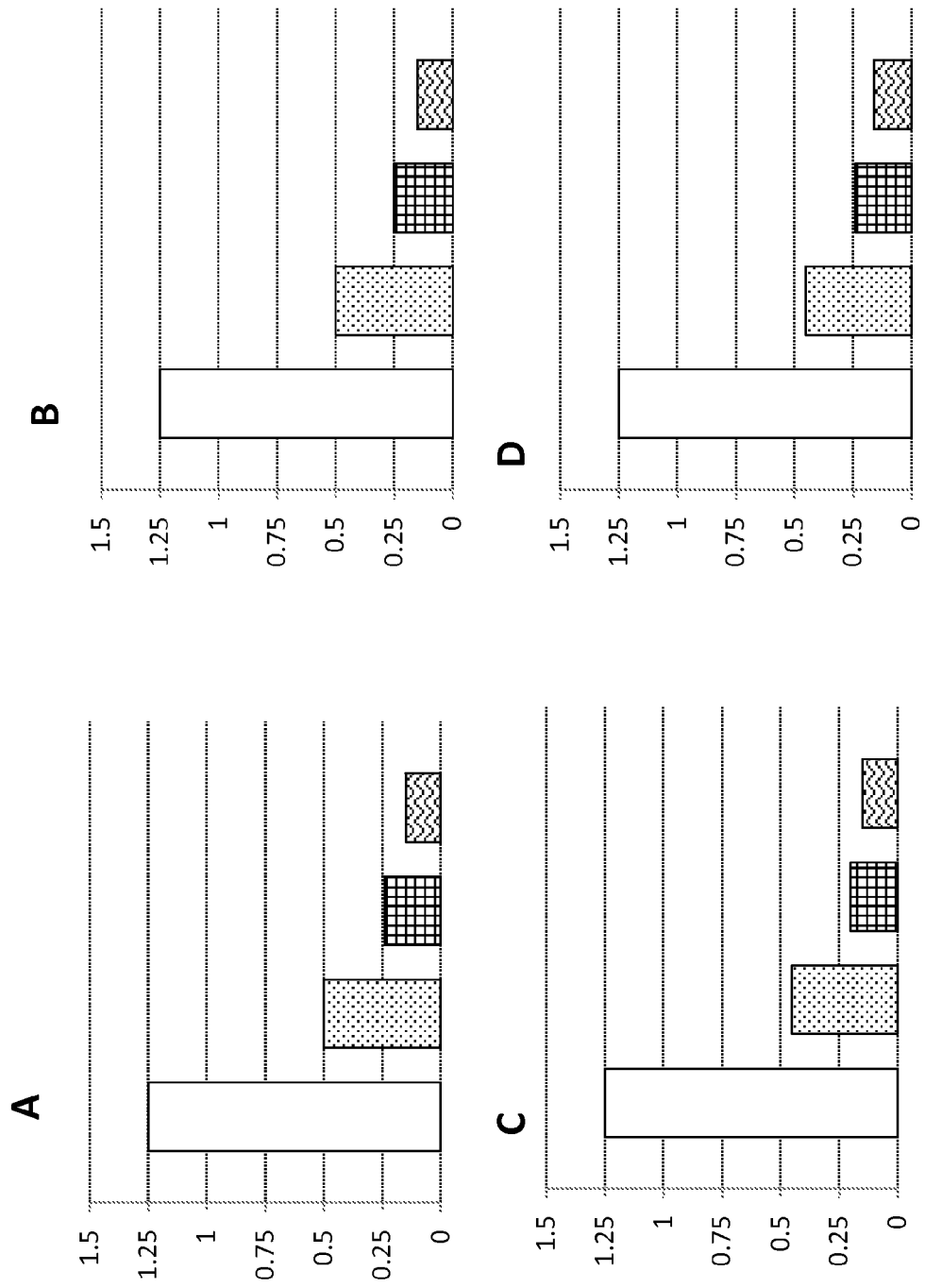
FIG. 1 shows histograms that demonstrate the potentiating effect of chemotherapy (assessed as an antiproliferative effect) by 2,5-dihydroxybenzene sulfonic acid, with different cytostatic compounds, (Panel A), Cisplatin (5 µg/ml); (Panel B), Vincristine (0.1 µl/ml); (Panel C), Paclitaxel (5 Ug/ml) and (Panel D), 5-fluorouracil (100 µg/ml). Ordinates: Absorbance 595 nm; Abscises: white histogram (control); dotted (cytostatic compound; day 1); lined histogram (2,5-dihydroxybenzene sulfonic acid+cytostatic compound; day 1); square histogram (2,5-dihydroxybenzene sulfonic acid (day 0)+cytostatic compound; day 1).

As used throughout the disclosure, the following terms, unless otherwise indicated, shall be understood to have the following meanings.

"Patient" refers to animals, preferably mammals, most preferably humans, and includes males and females, and children and adults.

"Effective amount" refers to the amount of the compound and/or compositions that is effective to achieve its intended purpose.

"Treating," "treat" or "treatment" refers to using the compounds or compositions of the present invention either prophylactically to prevent the symptoms of the disease or disorder, or therapeutically to ameliorate an existing condition.

"Cancer" refers to a disease or disorder characterized by the uncontrolled division of cells and the ability of those cells to invade other tissues, either by direct growth into adjacent tissue through invasion or by implantation into distant sites by metastasis.

"Skin cancer" refers to and includes, basal cell carcinoma, squamous cell carcinoma, melanomas, keratoacanthoma, actinic keratosis, Bowen's disease, verrucae, sarcomas, angiosarcoma such as Kaposi's angiosarcoma and the like.

"Cancer of an organ" refers to and includes, breast cancer, bladder cancer, colon cancer, rectal cancer, endometrial cancer, kidney cancer, lung cancer, cervical cancer, pancreatic cancer, prostate cancer, sweat gland carcinoma, sebaceous gland carcinoma, testicular cancer, thyroid cancer, ovarian cancer, Wilm's tumor, glioma, glioblastoma, meningioma, and the like.

"Leukemia" refers to and includes, blood borne cancers, such as, or example, acute lymphocytic leukemia; acute myelocytic leukemia, such as, myeloblastic, promyeloblastic, myelomonocytic, erythrocytic leukemia, and the like; chronic leukemia, such as, chronic myelocytic (granulocytic) leukemia, chronic lymphocytic leukemia, and the like; polycytemia vera, lymphoma (Hodgkin's disease and non-Hodgkin's disease), multiple myeloma, Waldenström's macroglobulinemia, heavy chain disease, and the like.

"Chemotherapy" refers to the use of a chemotherapeutic agent to treat a cancer.

"Radiation therapy" or "radiotherapy" refers to the medical use of ionization radiation as part of the treatment of cancer to control malignant cells.

"Cancer immunotherapy" refers to the stimulation of the immune system to reject or destroy tumours, and, includes, but is not limited to, BCG immunotherapy, topical immunotherapy, injection immunotherapy, and the like.

"Psoriasis" refers to and includes, immune-mediated diseases which affects the skin and joints. When it affects the skin it commonly appears as red scaly elevated patches called plaques. Psoriasis plaques are areas of inflammation and excessive skin cell production.

"Therapeutic agent" includes any therapeutic agent that can be used to treat or prevent the diseases described herein. "Therapeutic agents" include, but are not limited to, chemotherapeutic agents, steroids, retinoids, antimicrobial compounds, antioxidants, anti-inflammatory compounds, NMDA receptor antagonists, endothelin antagonists, immunomodulating agents, vitamin D analogues, salicylic acid, and the like. Therapeutic agent includes the pharmaceutically acceptable salts thereof, pro-drugs, and pharmaceutical derivatives thereof "Lower alkyl" refers to branched or straight chain acyclic alkyl group comprising one to about four carbon atoms. Exemplary lower alkyl groups include methyl, ethyl, n-propel, isopropyl, n-butyl, isobutyl, sec-butyl, t-butyl, and the like.

"Antimicrobial compound" refers to any compound that alters the growth of bacteria, fungi or virus whereby growth is prevented, modified, impaired, stabilized, inhibited or terminated. Antimicrobial compounds can be microbiocidal or microbiostatic and include, but are not limited to antibiotics, semisynthetic antibiotics, synthetic antibiotics, antifungal compounds, antiviral compounds, and the like.

"Antifungal compound" refers to any compound that alters the growth of fungi whereby growth is prevented, modified, impaired, stabilized, inhibited or terminated.

"Antiviral compound" refers to any compound that alters the growth of viral cells whereby growth is prevented, modified, impaired, stabilized, inhibited or terminated.

"Antioxidant" refers to and includes any compound that can react and quench a free radical including, but not limited to, free radical scavengers, iron chelators, small-molecule antioxidants and antioxidant enzymes, and the like.

"Taxane" refers to any compound that contains the carbon core framework represented by formula A:

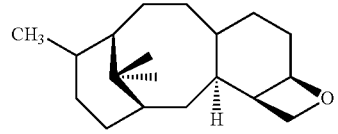

A

"NSAID" refers to a nonsteroidal anti-inflammatory compound or a nonsteroidal anti-inflammatory drug. NSAIDs inhibit cyclooxygenase, the enzyme responsible the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Organic cation" refers to a positively charged organic ion. Exemplary organic cations include alkyl substituted or unsubstituted ammonium cations, primary, secondary and tertiary amines, alkyl amines, aryl amines, cyclic amines, N,N'-dibenzylethylenediamine, and the like "Inorganic cation" refers to a positively charged metal ion. Exemplary inorganic cations include Group I metal cations, such as, for example, sodium, potassium, magnesium, calcium, and the like.

"Topical" refers to the delivery of a compound by application to the body surface and includes, but is not limited to, transdermal delivery and transmucosal delivery.

"Transdermal" refers to the delivery of a compound by passage through the skin and into the blood stream.

"Transmucosal" refers to delivery of a compound by passage of the compound through the mucosal tissue and into the blood stream.

"Parenteral" refers to delivery of a compound by subcutaneous, intravenous, intramuscular, intracardiac, intradermal, intraperitoneal, intrathecal or instrasternal injection and also includes infusion techniques.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Sustained release" refers to the release of an active compound and/or composition such that the blood levels of the active compound are maintained within a desirable therapeutic range over a period of time. The sustained release formulation can be prepared using any conventional method known to one skilled in the art to obtain the desired release characteristics.

In one embodiment, the invention describes the methods of use of 2,5-dihydroxybenzene sulfonic acid compounds of Formula (I) and pharmaceutically acceptable salts thereof:

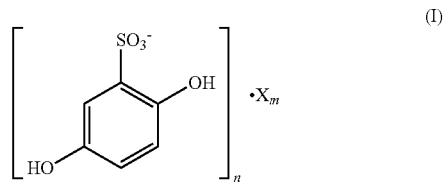

(I)

wherein:

X is a hydrogen, an organic cation or an inorganic cation;

n is an integer from 1 to 2; and m is an integer from 1 to 2.

The cation X in the 2,5-dihydroxybenzene sulfonic acid compounds of Formula (I) may be any physiologically acceptable cation known to one skilled in the art, and include, but are not limited to, those described in Heinrich Stahl, P., Camille G. Wermuth (Editors), "Handbook of Pharmaceutical Salts Properties, Selections and Use", Verlag Helvetica Chimica Acta, Zurich, Switzerland, Wiley-VCH, Weinheim, Germany, 2002; the disclosures of each of which are incorporated by reference herein in their entirety. The cation X is selected such that the overall charge of the 2,5-dihydroxybenzene sulfonic compounds of Formula I is neutral.

In one embodiment of the invention the inorganic cation ion is sodium, potassium, lithium, calcium or magnesium.

In another embodiment of the invention the organic cation is $[NH_{4-p}R_p]^+$:

wherein p at each occurrence is independently selected from an integer from 0 to 4; and R is a lower alkyl group.

In another embodiment of the invention, the organic cations are a diethylamine group $[H_2N^+(C_2H_5)_2]$, piperazine or pyridine.

In other embodiments of the invention, the compounds of Formula (I) are:

2,5-dihydroxybenzene sulfonic acid (dobesilate);

calcium 2,5-dihydroxybenzenesulfonate (calcium dobesilate);

potassium 2,5-dihydroxybenzenesulfonate (potassium dobesilate);

magnesium 2,5-dihydroxybenzenesulfonate (magnesium dobesilate); and diethylamine 2,5-dihydroxybenzenesulfonate (ethamsylate).

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the invention anticipates and includes within its scope all such isomers and mixtures thereof.

The 2,5-dihydroxybenzene sulfonic acid compounds of Formula (I) may also be in the form of solvates, particularly in the form of hydrates. The manufacture of the 2,5-dihydroxybenzene sulfonic acid compounds of Formula (I) as well as their solvates may be synthesized by one skilled in the art using conventional methods and commercially available reagents.

The compounds of Formulas (I) can be synthesized by one skilled in the art using conventional methods or are commercially available. The synthesis of the compounds of Formula (I) are disclosed in, for example, U.S. Pat. No. 5,082,941; and "The Merck Index" 13$^{th}$ edition, Merck & Co., R. Rahway, N.J., USA, 2001; the disclosures of each of which are incorporated by reference in their entirety.

The invention provides compositions comprising at least one compound of Formula (I) and at least one therapeutic agent, including, but not limited to, chemotherapeutic agents, steroids, retinoids, antimicrobial compounds, antioxidants, anti-inflammatory compounds, NMDA receptor antagonists, endothelin antagonists, immunomodulating agents, vitamin D analogues, salicylic acid, and combinations of two or more thereof. In one embodiment of the invention, the therapeutic agent does not include anti-inflammatory compounds. The invention also provides for such compositions in a pharmaceutically acceptable carrier.

The compounds of Formula (I) can optionally be used in combination with therapeutic agents; such as for example, chemotherapeutic agents, steroids, retinoids, antimicrobial compounds, antioxidants, anti-inflammatory compounds, NMDA receptor antagonists, endothelin antagonists, immunomodulating agents, vitamin D analogues, salicylic acid, and combinations of two or more thereof for treating skin cancer; treating cancer of the organs; treating leukemia; improving the efficacy of chemotherapy, radiation therapy and/or cancer immunotherapy; treating rosacea; and treating psoriasis.

Suitable chemotherapeutic agents, include, but are not limited to, alkylating agents, such as, for example, cyclophosphamide, carmustine, daunorubicin, mechlorethamine, chlorambucil, nimustine, mephalan, and the like; anthracyclines, such as, for example, daunorubicin, doxorubicin, epirubicin, idarubicin, mitoxantrone, valrubicin, and the like; taxane compounds, such as, for example, pacitaxel, docetaxel, and the like; topoisomerase inhibitors, such as, for example, eloposide, teniposide, taluposide, and the like; nucleotide analogs, such as, for example, azacitidine, azathioprine, capecitabine, cytarabine, doxifluridine, fluorouracil, gemcitabine, mercaptopurine, methotrexate, tioguanine, and the like; platinum based agents, such as, for example, carboplatin, cisplatin, oxaliplatin, and the like; antineoplatic agents, such as, for example, vincristine, leucovorin, lomustine, procarbazine, and the like; hormonal modulators, such as, for example, tamoxifen, finasteride, 5-α-reductase inhibitors, and the like; vinca alkaloids, such as for example, vinblastin, vincristine, vindesine, vinorelbine, and the like. Suitable chemotherapeutic agents are described more fully in the literature, such as in the Merck Index on CD-ROM, 13$^{th}$ Edition.

In some embodiments of the invention the chemotherapeutic agents are 5-fluorouracil, tamoxifin, paclitaxel, cisplatin, carboplatin, carmustine, nimustine, leucovorin, gemcitabine, docetaxel, vincristin, vinblastin, vinorelbine, vindesine, irinotecan, vinca alkaloids or topoisomerase inhibitors.

Suitable steroids, include, but are not limited to, budesonide, dexamethasone, corticosterone, prednisolone, and the like. Suitable steroids are described more fully in the literature, such as in the Merck Index on CD-ROM, 13$^{th}$ Edition.

In one embodiment of the invention the steroids are dexamethasone, prednisolone and corticosteroids.

Suitable retinoids, include, but are not limited to, natural and synthetic analogs of vitamin A (retinol), vitamin A aldehyde (retinal), vitamin A acid (retinoic acid (RA)), including all trans, 9-cis, and 12-cis retinoic acid), tretinoin, isotretinoin, alitretinoin, etretinate, acitrtin, tazarolene, bexarotene, and the like. Suitable retinoids are also disclosed in EP 0379367 A2, U.S. Pat. Nos. 4,887,805, 4,888,342, 5,514,825; 5,698,700; 5,696,162; 5,688,957; 5,677,451; 5,677,323; 5,677,320; 5,675,033; 5,675,024; 5,672,710; 5,688,175; 5,663,367; 5,663,357; 5,663,347; 5,648,514; 5,658,503; 5,618,943; 5,618,931; 5,618,836; 5,605,915; 5,602,130, 5,648,563; 5,648,385; 5,618,839; 5,559,248; 5,616,712; 5,616,597; 5,602,135; 5,599,819; 5,556,996; 5,534,516; 5,516,904; 5,498,755; 5,470,999; 5,468,879; 5,455,265; 5,451,605; 5,343,173; 5,426,118; 5,414,007; 5,407,937; 5,399,586; 5,399,561; 5,391,753, and the like; the disclosures of each of which are incorporated by reference herein in their entirety.

In some embodiments of the invention the retinoids are retinol, retinal, retinoic acid, tretinoin, isotretinoin or alitretinoin.

Suitable antimicrobial compounds, include, but are not limited to, macrolides, such as, for example, azithromycin, clarithromycin, dirithromycin, erythromycin, milbemycin, troleandomycin, and the like; monbactams, such as, for example, azetreonam, and the like;

Tetracyclins, such as, for example, demeclocyclin, doxycycline, minocycline, oxytetracyclin, tetracycline, and the like; aminoglycosides, such as, for example, amikacin, gentamicin, kanamycin, neomycin, netilmiein, paromomycin, streptomycin, tobramycin, and the like; carbacephem, such as, for example, loracarbef, and the like; carbapenems, such as, for example, ertapenem, imipenem, meropenem, and the like; penicillins, such as, for example, amoxicillin, ampicillin, azlocillin, carbenicillin, cloxacillin, dicloxacillin, flucloxacillin, mezlocillin, nafcillin, penicillin, piperacillin, ticarcillin, and the like; polypeptides, such as, for example, bacitracin, colistin, polymyxin B, and the like; beta-lactamase inhibitors; cephalosporins, such as, for example, cefaclor, cefamandole, cefoxitin, cefprozil, cefuroxime, cefixime, cefdinir, cefditoren, cefoperazone, cefotaxime, cefpodoxime, cefadroxil, ceftazidime, ceftibuten, ceflizoxime, ceftiriaxone, cefazolin, cefixime, cephalexin, cefepime, and the like; quinolones, such as, for example, ciprofloxacin, enoxacin, gatifloxacin, levofloxacin, lomefloxacin, morifloxacin, norfloxacin, ofloxacin, trovafloxacin, and the like; streptogramins; sulfonamides, such as, for example, mefanide, prontosil, sulfacetamide, sulfamethizole, sulfanilamide, sulfasalazine, sulfisoxazole, trimethoprim, trimethoprim-sultamethoxazole, and the like; and the combination drugs such as for example, sulfamethoxazole and trimethoprim, and the like. Suitable antimicrobial compounds of the invention are described more fully in the literature, such as in Goodman and Gilman, The Pharmacological Basis of Therapeutics (9th Edition), McGraw-Hill, (1996); Merck Index on CD-ROM, 13$^{th}$ Edition; STN Express, file phar and file registry, the disclosures of each of which are incorporated by reference herein in their entirety.

In some embodiments of the invention, the antimicrobial compounds are tetracycline, erythromycin or clindamycin.

Suitable antioxidants include, but are not limited to, free radical scavengers, iron chelators, small-molecule antioxidants and antioxidant enzymes, and the like. Suitable iron chelators include, but are not limited to, deferoxamine, deferiprone, dithiocarbamatem, ethylene diamine tetraacetic acid, and the like. Suitable small-molecule antioxidants include, but are not limited to, hydralazine compounds, glutathione, ascorbic acid (vitamin C), vitamin E, cysteine, N-acetyl-cysteine, β-carotene, ubiquinone, ubiquinol-10, tocopherols, coenzyme Q, superoxide dismutase mimetics, such as, for example, 2,2,6,6-tetramethyl-1-piperidinyloxy (TEMPO), DOXYL, PROXYL nitroxide compounds; 4-hydroxy-2,2,6,6-tetramethyl-1-piperidinyloxy (Tempol), M-40401, M-40403, M-40407, M-40419, M-40484, M-40587, M-40588, and the like. Suitable antioxidant enzymes include, but are not limited to, superoxide dismutase, catalase, glutathione peroxidase, NADPH oxidase inhibitors, such as, for example, apocynin, aminoguanidine, ONO 1714, S17834 (benzo(b)pyran-4-one derivative), and the like; xanthine oxidase inhibitors, such as, for example, allopurinol, oxypurinol, amflutizole, diethyldithiocarbamate, 2-styrylchromones, chrysin, luteolin, kaempferol, quercetin, myricetin, isorhamnetin, benzophenones such as 2,2', 4,4'-tetrahydroxybenzophenone, 3,4,5,2',3',4'-hexahydroxybenzophenone and 4,4'-dihydroxybenzophenone; benzothiazinone analogues such as 2-amino-4H-1,3-benzothiazine-4-one, 2-guanidino-4H-1,3-benzothiazin-4-one and rhodanine; N-hydroxyguanidine derivative such as, PR5 (1-(3,4-dimethoxy-2-chlorobenzylideneamino)-3-hydroxyguanidine); 6-formylpterin, and the like. The antioxidant enzymes can be delivered by gene therapy as a viral vector and/or a non-viral vector. Suitable antioxidants are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the antioxidants are ascorbic acid, Vitamin E, apocynin, hydralazine compounds or superoxide dimutase mimetics.

Suitable NSAIDs include, but are not limited to, acetaminophen, acemetacin, aceclofenac, alminoprofen, amfenac, bendazac, benoxaprofen, bromfenac, bucloxic acid, butibufen, carprofen, cinmetacin, clopirac, diclofenac, etodolac, felbinac, fenclozic acid, fenbufen, fenoprofen, fentiazac, flunoxaprofen, flurbiprofen, ibufenac, ibuprofen, indomethacin, isofezolac, isoxepac, indoprofen, ketoprofen, lonazolac, loxoprofen, metiazinic acid, mofezolac, miroprofen, naproxen, oxaprozin, pirozolac, pirprofen, pranoprofen, protizinic acid, salicylamide, sulindac, suprofen, suxibozone, tiaprofenic acid, tolmetin, xenbucin, ximoprofen, zaltoprofen, zomepirac, aspirin, acemetcin, bumadizon, carprofenac, clidanac, diflunisal, enfenamic acid, fendosal, flufenamic acid, flunixin, gentisic acid, ketorolac, meclofenamic acid, mefenamic acid, mesalamine, prodrugs thereof, and the like. Suitable NSAIDs are described more fully in the literature, such as in Goodman and Gilman, The Pharmacological Basis of Therapeutics (9th Edition), McGraw-Hill, 1995, Pgs. 617-657; the Merck Index on CD-ROM, 13$^{th}$ Edition; and in U.S. Pat. Nos. 6,057,347 and 6,297,260 assigned to NitroMed Inc., the disclosures of which are incorporated herein by reference in their entirety.

In some embodiments the NSAIDs are acetaminophen, diclofenac, flurbiprofen, ibuprofen, indomethacin, ketoprofen, naproxen or aspirin.

Suitable N-methyl-D-aspartate (NMDA) receptor antagonists, include, but are not limited to, ketamine, dextromethorphan, memantine, amantadine, nitrous oxide, Gacyclidine and the like.

In some embodiments the NMDA receptor antagonists are dextromethorphan.

Suitable endothelin antagonists include, but are not limited to, atrasentan, bosentan, darusentan, enrasentan, sitaxsentan, sulfonamide endothelin antagonists, tezosentan, BMS 193884, BQ-123, SQ 28608, and the like. Suitable endothelin antagonists are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable immunomodulating agents, include, but are not limited to, interferon α IIb, autologous granulocyte macrophagecolony stimulating factor, APC 8015 (Provenge), cancer vaccines, anti-sense oligonucleotides, bacillus or Calmette-Guerin (BCG), and the like.

Suitable vitamin D analogues, include but are not limited to, vitamin D3 analogues such as, cholecalciferol, calcidiol, calcitriol, and the like.

The invention describes methods for treating skin cancer; treating cancer of an organ; treating leukemia; and improving the efficacy of chemotherapy, radiation therapy and/or cancer immunotherapy in a patient in need thereof comprising administering to the patient in need thereof an effective amount of the compounds and/or compositions described herein. For example, the patient can be administered an effective amount of at least one 2,5-dihydroxybenzene sulfonic acid compound. In another embodiment, the patient can be administered an effective amount of at least one 2,5-dihydroxybenzene sulfonic acid compound, and, at least one therapeutic agent, including but not limited to, such as, for example, chemotherapeutic agents, steroids, retinoids, antimicrobial compounds, antioxidants, anti-inflammatory compounds, NMDA receptor antagonists, endothelin antagonists, immunomodulating agents, vitamin D analogues, salicylic acid, and combinations of two or more thereof. The 2,5-dihydroxybenzene sulfonic acid compounds and/or therapeutic agents can be administered separately or as components of the same composition in one or more pharmaceutically acceptable carriers.

In one embodiment of the invention for the methods for treating skin cancer; treating cancer of an organ; treating leukemia; and improving the efficacy of chemotherapy, radiation therapy and/or cancer immunotherapy the therapeutic agent is selected from the group consisting of chemotherapeutic agents, steroids, antimicrobial compounds, antioxidants, anti-inflammatory compounds, NMDA receptor antagonists, endothelin antagonists, immunomodulating agents, and combinations of two or more thereof.

The invention describes methods for treating rosacea in a patient in need thereof comprising topically administering to the patient in need thereof an effective amount of the compounds and/or compositions described herein. For example, the patient can be administered an effective amount of at least one 2,5-dihydroxybenzene sulfonic acid compound. In another embodiment, the patient can be administered an effective amount of at least one 2,5-dihydroxybenzene sulfonic acid compound, and, at least one therapeutic agent, including, but not limited to, such as, for example, steroids, retinoids, antimicrobial compounds, antioxidants, anti-inflammatory compounds, and combinations of two or more thereof. The 2,5-dihydroxybenzene sulfonic acid compounds and/or therapeutic agents can be administered separately or as components of the same composition in one or more pharmaceutically acceptable carriers.

In one embodiment of the invention for the methods for treating rosacea the therapeutic agent is selected from the group consisting of steroids, retinoids, antimicrobial compounds, antioxidants, anti-inflammatory compounds, vitamin D analogues, salicylic acid, and combinations of two or more thereof.

The invention describes methods for treating psoriasis in a patient in need thereof comprising administering to the patient in need thereof an effective amount of the compounds and/or compositions described herein. For example, the patient can be administered an effective amount of at least one 2,5-dihydroxybenzene sulfonic acid compound. In another embodiment, the patient can be administered an effective amount of at least one 2,5-dihydroxybenzene sulfonic acid compound, and, at least one therapeutic agent, including but not limited to, such as, for example, steroids, retinoids, antimicrobial compounds, antioxidants, anti-inflammatory compounds, and combinations of two or more thereof. The 2,5-dihydroxybenzene sulfonic acid compounds and/or therapeutic agents can be administered separately or as components of the same composition in one or more pharmaceutically acceptable carriers.

In one embodiment of the invention for the methods for treating psoriasis the therapeutic agent is selected from the group consisting of steroids, retinoids, antimicrobial compounds, antioxidants, anti-inflammatory compounds, vitamin D analogues, salicylic acid, and combinations of two or more thereof.

When administered separately, the 2,5-dihydroxybenzene sulfonic acid compound, can be administered about the same time as part of the overall treatment regimen i.e., as a combination therapy. "About the same time" includes administering the 2,5-dihydroxybenzene sulfonic acid compound, simultaneously, sequentially, at the same time, at different times on the same day, or on different days, as long as they are administered as part of an overall treatment regimen, i.e., combination therapy or a therapeutic cocktail.

When administered in vivo, the compounds and compositions of the invention can be administered in combination with pharmaceutically acceptable carriers and in dosages described herein. When the compounds and compositions of the invention are administered as a combination of at least one 2,5-dihydroxybenzene sulfonic acid compound and/or at least one therapeutic agent, they can also be used in combination with one or more additional compounds which are known to be effective against the specific disease state targeted for treatment. The therapeutic agents and/or other additional compounds can be administered simultaneously with, subsequently to, or prior to administration of the 2,5-dihydroxybenzene sulfonic acid compound.

The compounds and compositions of the invention can be administered by any available and effective delivery system including, but not limited to, orally, bucally, parenterally, by inhalation, by topical application, or rectally (e.g., by the use of suppositories) in dosage unit formulations containing conventional nontoxic pharmaceutically acceptable carriers, adjuvants, and vehicles, as desired.

In one embodiment of the invention the 2,5-dihydroxybenzene sulfonic acid compounds of the invention are administered orally, bucally, parenterally, by inhalation, by topical application or rectally for the treatment of skin cancer; cancer of an organ; leukemia; and improving the efficacy of chemotherapy, radiation therapy and/or cancer immunotherapy. In another embodiment of the invention the 2,5-dihydroxybenzene sulfonic acid compounds are administered orally, parenterally or by topical application for the treatment of skin cancer or improving the efficacy of chemotherapy, radiation therapy and/or cancer immunotherapy. In yet another embodiment of the invention the 2,5-dihydroxybenzene sulfonic acid compounds are administered orally, bucally, parenterally or by topical application for the treatment of cancer of an organ. In one embodiment of the invention the 2,5-dihydroxybenzene sulfonic acid compounds are administered orally, bucally or parenterally for the treatment of leukemia.

In some embodiments of the invention the 2,5-dihydroxybenzene sulfonic acid compounds are administered orally, bucally, parenterally or topically for the treatment of psoriasis.

Solid dosage forms for oral administration can include capsules, sustained-release capsules, tablets, sustained release tablets, chewable tablets, sublingual tablets, effervescent tablets, pills, suspensions, powders, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention can be prepared by mixing the compounds or compositions with a suitable nonirritating excipient such as cocoa butter and polyethylene glycols which are solid at room temperature but liquid at rectal temperature, such that they will melt in the rectum and release the compounds and compositions.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspensions in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

Topical administration of the compounds and compositions invention can be in the form of creams, gels, lotions, liquids, ointments, sprays solution, dispersions, solid sticks, emulsions, microemulsions, eye drops, nose drops, ear drops, and the like, that can be formulated according to the conventional methods using suitable excipients, such as, for example, emulsifiers, surfactants, thickening agents, sunscreen agents, moisturizers, cooling agents, skin lightening agent, skin conditioning agents, skin protectants, emollients, humectants, colorants, and combinations of two or more thereof The compounds and compositions of the invention can be transdermally administered in the form of transdermal patches or iontophoresis devices. Other components can optionally be incorporated into the transdermal patches. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Woven pads or rolls of bandaging material, e.g., gauze, can be impregnated with the compositions in solution, lotion, cream, ointment or other such form can also be used for topical application. In one embodiment, the compositions of the invention are administered as a transdermal patch. In another embodiment compositions of the invention are administered as a sustained-release transdermal patch. The transdermal patches of the invention can include any conventional forms such as, for example, adhesive matrix, polymeric matrix, reservoir patch, matrix or monolithic-type laminated structure, and are generally comprised of one or more backing layers, adhesives, penetration enhancers, an optional rate controlling membrane and a release liner which is removed to expose the adhesives prior to application. Polymeric matrix patches also comprise a polymeric-matrix forming material. Suitable transdermal patches are described in more detail in, for example, U.S. Pat. Nos. 5,262,165, 5,948,433, 6,010,715 and 6,071,531, the disclosure of each of which are incorporated herein in their entirety.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

Suitable sustained-release forms as well as the materials and methods for their preparation are described in, for example, "Modified-Release Drug Delivery Technology", Rathbone, M. J. Hadgraft, J. and Roberts, M. S. (Eds.), Marcel Dekker, Inc. New York (2002); "Handbook of Pharmaceutical Controlled Release Technology", Wise, D. L. (Ed.), Marcel Dekker, Inc. New York, (2000); "Controlled Drug Delivery", Vol. 1, Basic Concepts, Bruck, S. D. (Ed.), CRC Press Inc., Boca Raton (1983) and from Takada, K. and Yoshikawa, H., "Oral Drug delivery", Encyclopedia of Controlled Drug Delivery, Mathiowitz, E. (Ed.), John Wiley & Sons, Inc., New York (1999), Vol. 2, 728-742; Fix, J., "Oral drug delivery, small intestine and colon", Encyclopedia of Controlled Drug Delivery, Mathiowitz, E. (Ed.), John Wiley & Sons, Inc., New York (1999), Vol. 2, 698-728; the disclosures of each of which are incorporated herein by reference in their entirety.

In one embodiment of the invention, the orally administrable form of the 2,5-dihydroxybenzene sulfonic acid compounds is in a sustained-release form further comprising at least one coating or matrix. The sustained-release coating or matrix, include, but are not limited to, modified, water-insoluble, natural, semisynthetic or synthetic polymers, natural, semisynthetic or synthetic waxes, fats, fatty alcohols, fatty acid, plasticizers, or a combination of two or more thereof.

Suitable water-insoluble polymers, include, but are not limited to, acrylic resins, such as, for example, poly(meth)acrylates, poly($C_{1-4}$) alkyl(meth)acrylates, poly($C_{1-4}$)dialkylamino ($C_{1-4}$) alkyl(meth)acrylates and/or copolymers, and the like, and combinations of two or more thereof; copolymers of ethyl acrylate and methyl methacrylate with a monomer molar ratio of 2:1 (EUDRAGIT NE30D®), copolymers of ethyl acrylate, methylmethacrylate and trimethylammonium ethyl methacrylate-chloride with a monomer molar ratio of 1:2:0.1 (EUDRAGIT RS®), copolymers of ethyl acrylate, methyl methacrylate and trimethylammonium ethyl methacrylate-chloride with a monomer molar ratio of 1:2:0.2 (EUDRAGIT RL®), and the like, and combinations of two or more thereof.

Suitable water-insoluble polymers, include, but are not limited to, cellulose derivatives, such as, for example, alkyl celluloses, ethyl cellulose, cellulose esters, cellulose acetate, AQUACOAT®, SURELEASE®, and the like.

Suitable natural, semisynthetic or synthetic waxes, fats or fatty alcohols, include, but are not limited to, carnauba wax, beeswax, glycerol monostearate, glycerol monobehenate, glycerol ditripalmitostearate, microcrystalline wax, cetyl alcohol, cetylstearyl alcohol, and the like, and combinations of two or more thereof.

Suitable plasticizers, include, but are not limited to, lipophilic diesters of a $C_6$-$C_{40}$ aliphatic or aromatic dicarboxylic acids, $C_1$-$C_8$ aliphatic alcohols, such as, for example, dibutyl phthalate, diethyl phthalate, dibutyl sebacate, diethyl sebacate, and the like; hydrophilic or lipophilic citric acid esters, such as, for example, trietyl citrate, tributyl citrate, acetyltributyl citrate, acetyltriethyl citrate, and the like; polyethylene glycols, propylene glycol, glycerol esters, such as, for example, triacetin, MYVACET® (acetylated mono- and diglycerides, $C_{23}H_{44}O_5$ to $C_{25}H_{47}O$), medium-chain triglycerides (MIGLYOL®), oleic acid or mixtures of at least two of said plasticizers. The sustained-release formulations may comprise one or more plasticizers in amounts of, about 5 to about 50 wt. % based on the amount of polymer(s) used.

The sustained-release formulations may also contain other conventional excipients known to one skilled in the art, such as, for example, lubricants, colored pigments, surfactants, and the like. The sustained-release formulations may also contain an enteric coating.

Suitable enteric coatings, include, but are not limited to, methacrylic acid/methyl methacrylate copolymers with a monomer molar ratio of 1:1 (EUDRAGIT L®), methacrylic acid/methyl methacrylate copolymers with a monomer molar ratio of 1:2 (EUDRAGIT S®), methacrylic acid/ethyl acrylate copolymers with a monomer molar ratio of 1:1 (EUDRAGIT L30D-55®), methacrylic acid/methyl acrylate/methyl methacrylate copolymers with a monomer molar ratio of 7:3:1 (EUDRAGIT FS®), shellac, hydroxypropyl methyl cellulose, acetate-succinates, cellulose acetate-phthalates or a combination of two or more thereof. These enteric coating can optionally also be used in combination with the water-insoluble poly (meth) acrylates described herein. In one embodiment the enteric coatings are used in combination with EUDRAGIT NE30D®, and/or EUDRAGIT RL® and/or EUDRAGIT RS®.

The enteric coatings may be applied using conventional processes known to those skilled in the art, as described in, for example, Johnson, J. L., "Pharmaceutical tablet coating", Coatings Technology Handbook (Second Edition), Salas, D. and Tracton, A. A. (Eds.), Marcel Dekker, Inc. New York, (2001), 863-866; Carstensen, T., "Coating Tablets in Advanced Pharmaceutical Solids", Swarbrick, J. (Ed.), Marcel Dekker, Inc. New York (2001), 455-468; Leopold, C. S., "Coated dosage forms for colon-specific drug delivery", Pharmaceutical Science & Technology Today, 2 (5), 197-204 (1999), Rhodes, C. T. and Porter, S. C. Coatings, in Encyclopedia of Controlled Drug Delivery. Mathiowitz, E. (Ed.), John Wiley & Sons, Inc., New York (1999), Vol. 1, 299-311; the disclosures of each of which are incorporated herein by reference in their entirety.

In one embodiment of the invention, the sustained release formulations comprising at least one 2,5-dihydroxybenzene sulfonic acid compound is in an immediate release form and in a sustained release form in the same formulation. The formulation may further comprises at least one therapeutic agent, such as for example, chemotherapeutic agents, steroids, retinoids, antimicrobial compounds, antioxidants, anti-inflammatory compounds, NMDA receptor antagonists, endothelin antagonists, immunomodulating agents, vitamin D analogues, salicylic acid, and combinations of two or more thereof.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given 2,5-dihydroxy benzene sulfonic acid compound that will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993; the disclosures of each of which are incorporated herein by reference in their entirety. The precise dose to be used in the formulation will also depend on the route of administration, and the seriousness of the disease or disorder, and should be decided by the physician and the patient's circumstances.

In one embodiment, the 2,5-dihydroxybenzene sulfonic acid compounds of Formula (I) can be orally, bucally or parentally administered in an amount of about 0.05 g per day to about 50 g per day. In particular embodiments, the 2,5-dihydroxybenzene sulfonic acid compounds of Formula (I) can be orally, bucally or parentally administered in an amount of about 0.10 g per day to about 25 g per day. In more particular embodiments, the 2,5-dihydroxybenzene sulfonic acid compounds of Formula (I) can be orally, bucally or parentally administered in an amount of about 0.25 g per day to about 10 g per day. In a more particular embodiment, 2,5-dihydroxybenzene sulfonic acid compounds of Formula (I) can be administered in an amount of about 0.5 g per day to about 5 g per day. In an even more particular embodiment, 2,5-dihydroxybenzene sulfonic acid compounds of Formula (I) can be administered in an amount of about 0.75 g per day to about 2.5 g per day. In another particular embodiment, 2,5-dihydroxybenzene sulfonic acid compounds of Formula (I) can be administered in an amount of about 1 g per day to about 1.5 g per day. The particular amounts of the 2,5-dihydroxybenzene sulfonic acid compounds of Formula (I) can be administered can be administered as a single dose once a day; or in multiple doses several times throughout the day; or as a sustained-release oral formulation. In one embodiment of the invention the 2,5-dihydroxybenzene sulfonic acid compounds of Formula (I) is administered orally, bucally or parentally as about 50 g, 25 g, 10 g, 5 g, 1 g, 0.75 g, 0.5 g, 0.25 g or 0.1 g once per day (q.d). In another embodiment of the invention the 2,5-dihydroxybenzene sulfonic acid compounds of Formula (I) is administered orally, bucally or parentally as about 50 g, 25 g, 10 g, 5 g, 1 g, 0.75 g, 0.5 g, 0.25 g or 0.1 g twice per day (b.i.d). In yet another embodiment of the invention the 2,5-dihydroxybenzene sulfonic acid compounds of Formula (I) is administered orally, bucally or parentally as about 50 g, 25 g, 10 g, 5 g, 1 g, 0.75 g, 0.5 g, 0.25 g or 0.1 g three times per day (t.i.d.). In another embodiment of the invention the 2,5-dihydroxybenzene sulfonic acid compounds of Formula (I) is administered orally, bucally or parentally as about 50 g, 25 g, 10 g, 5 g, 1 g, 0.75 g, 0.5 g, 0.25 g or 0.1 g four times per day.

In particular embodiments, the 2,5-dihydroxybenzene sulfonic acid compounds of Formula (I) can be topically administered in a formulation comprising an amount of about 0.001% to about 30% (w/w) of the 2,5-dihydroxybenzene sulfonic acid compounds of Formula (I). In a more particular embodiment, the 2,5-dihydroxybenzene sulfonic acid compounds of Formula (I) can be topically administered in a formulation comprising an amount of about 0.01% to about 20% (w/w) of the 2,5-dihydroxybenzene sulfonic acid compounds of Formula (I). In an even more particular embodiment, the 2,5-dihydroxybenzene sulfonic acid compounds of Formula (I) can be topically administered in a formulation comprising an amount of about 0.1% to about 15% (w/w) of the 2,5-dihydroxybenzene sulfonic acid compounds of Formula (I). In a more particular embodiment, the 2,5-dihydroxybenzene sulfonic acid compounds of Formula (I) can be topically administered in a formulation comprising an amount of about 0.5% to about 10% (w/w) of the 2,5-dihydroxybenzene sulfonic acid compounds of Formula (I). In another particular embodiment, the 2,5-dihydroxybenzene sulfonic acid compounds of Formula (I) can be topically administered in a formulation comprising an amount of about 1% to about 5% (w/w) of the 2,5-dihydroxybenzene sulfonic acid compounds of Formula (I). In a more particular embodiment, the 2,5-dihydroxybenzene sulfonic acid compounds of Formula (I) can be topically administered in a formulation comprising an amount of about 2.5% to about 4% (w/w) of the 2,5-dihydroxybenzene sulfonic acid compounds of Formula (I). The topical formulation comprising the 2,5-dihydroxybenzene sulfonic acid compounds of Formula (I) can be administered as a single dose once a day; or in multiple doses several times throughout the day. In one embodiment of the invention the topical formulation comprising about 30%, 20%, 15%, 10%, 5%, 2.5%, 1%, 0.5%, 0.1% or 0.001% of the 2,5-dihydroxybenzene sulfonic acid compounds of Formula (I) is administered four times per day. In another embodiment of the invention the topical formulation comprising about 30%, 20%, 15%, 10%, 5%, 2.5%, 1%, 0.5%, 0.1% or 0.001% of the 2,5-dihydroxybenzene sulfonic acid compounds of Formula (I) is administered three times per day (t.i.d). In yet another embodiment of the invention the topical formulation comprising about 30%, 20%, 15%, 10%, 5%, 2.5%, 1%, 0.5%, 0.1% or 0.001% of the 2,5-dihydroxybenzene sulfonic acid compounds of Formula (I) is administered two times per day (b.i.d). In another embodiment of the invention the topical formulation comprising about 30%, 20%, 15%, 10%, 5%, 2.5%, 1%, 0.5%, 0.1% or 0.001% of the 2,5-dihydroxybenzene sulfonic acid compounds of Formula (I) is administered once times per day (qd).

EXAMPLES

The following non-limiting examples further describe and enable one of ordinary skill in the art to make and use the present invention.

In all the examples, 2,5-dihydroxybenzene sulfonate (DHBS) refers to the potassium salt of 2,5-dihydroxybenzene sulfonic acid.

Example 1

2,5-Dihydroxybenzene Sulfonic Acid Potentiates Chemotherapy

C6 cells cultured in vitro under the same conditions as described in PCT Application No. 2005/077352. 1. $1 \times 10^3$ cells per well were cultured in 24-well plates. Three types of treatment were conducted: a) 24 hours after seeding, the cells were separately treated with each of the following medicines; cisplatin (5 µg/ml), vincristine (0.1 µg/ml), paclitaxel (5 µg/ml) and 5-fluorouracil (100 µg/ml); b) 24 hours after seeding, the cells were treated with a combination of 2,5-dihydroxybenzene sulfonic acid (100 µM) and each one of the following agents; cisplatin (5 µg/ml) vincristine (0.1 µg/ml), paclitaxel (5 µg/ml) and 5-fluorouracil (100 µg/ml); c) at the time of seeding (Day 0), the cells were pre-treated with 2,5-dihydroxybenzene sulfonic acid (100 µM). The next day the cultures were also treated with each one of the following agents: cisplatin (5 µg/ml) vincristine (0.1 µg/ml), paclitaxel (5 µg/ml) and 5-fluorouracil (100 µg/ml). The controlled cultures did not receive any treatment for 2 days. After 48 hours (day 2), the cells were evaluated in all the cultures. This study was carried out in triplicate independent experiments and was repeated three times.

FIG. 1 (A, B, C and D) shows the histograms of the experiments performed to evaluate the effect of the 2,5-dihydroxybenzene sulfonic acid to potentate cytostatic agents. Treatment with cysplatin, vincristine and 5-fluorouracil produced an inhibition of 50% in the proliferation of C6 cells, while treatment with paclitaxel resulted in 67% inhibition of the cellular proliferation. The treatment with the combination of the 2,5-dihydroxybenzene sulfonic acid and the cytostatic agents (cysplatin, vincristine and 5-fluorouracil) resulted in an 84% inhibition in cellular proliferation. The combination treatment with 2,5-dihydroxybenzene sulfonic acid and paclitaxel resulted in 86% inhibition of the cellular proliferation. When the cellular cultures were pre-treated with the 2,5-dihydroxybenzene sulfonic acid followed by the cytostatic agents: cysplatin, vincristine and 5-fluorouracil, 90% inhibition was obtained in the cell proliferation. When paclitaxel was used, the inhibition in cellular proliferation was up to 92%.

The results demonstrate that the simultaneous treatment of the 2,5-dihydroxybenzene sulfonic acid with the chemotherapeutic agents, increases their therapeutic efficacy and the chemical potentiation effect is higher when the cells have been pre-treated with 2,5-dihydroxybenzene sulfonic acid. These data support the use of the 2,5-dihydroxybenzene sulfonic acid as an aid in the treatment associated with chemical therapy and radiotherapy.

Example 2

2,5-Dihydroxybenzene Sulfonate Increases the Chemo Sensitivity in Rat C6 Glioma Cells Cultures of rat glioma C6 cells were grown as described in Cuevas P et al. *Neurol. Res.*, 27: 797-800 (2005). Briefly, cells were grown as adherent cells in Dulbecco modified Eagle medium supplemented with 1% (v/v) fatal bovine serum, 10 µg/ml streptomycin and 10 units/ml penicillin (DMEM). Tumour cells were set up in 24-well cell culture plates, at a density of 10,000 cells per well and incubated at 37° C. in a humidified chamber with 5% $CO_2$. Cells were either treated with 2,5-dihydroxybenzene sulfonate (100 µM in DMEM) or with DMEM (controls). Eighty hours after the addition of 2,5-dihydroxybenzene sulfonate, the cells were either treated or not treated with the cytostatic agents, cisplatin (5 µg/ml in DMEM), vincristine (0.5 µg/ml in DMEM), paclitaxel (5 µg/ml in DMEM), 5-fluorouracil (100 µg/ml in DMEM) and irinotecan (CPT-11; 0.1 µg/ml in DMEM). After an additional two days the proliferation of the glioma cells was assessed using crystal violet staining of fixed cells. The cell number was computed by the amount of retained dye determined spectroscopically at 595 nm after its resolubilization. Cell viability was estimated by trypan blue dye assay.

Figure 2:
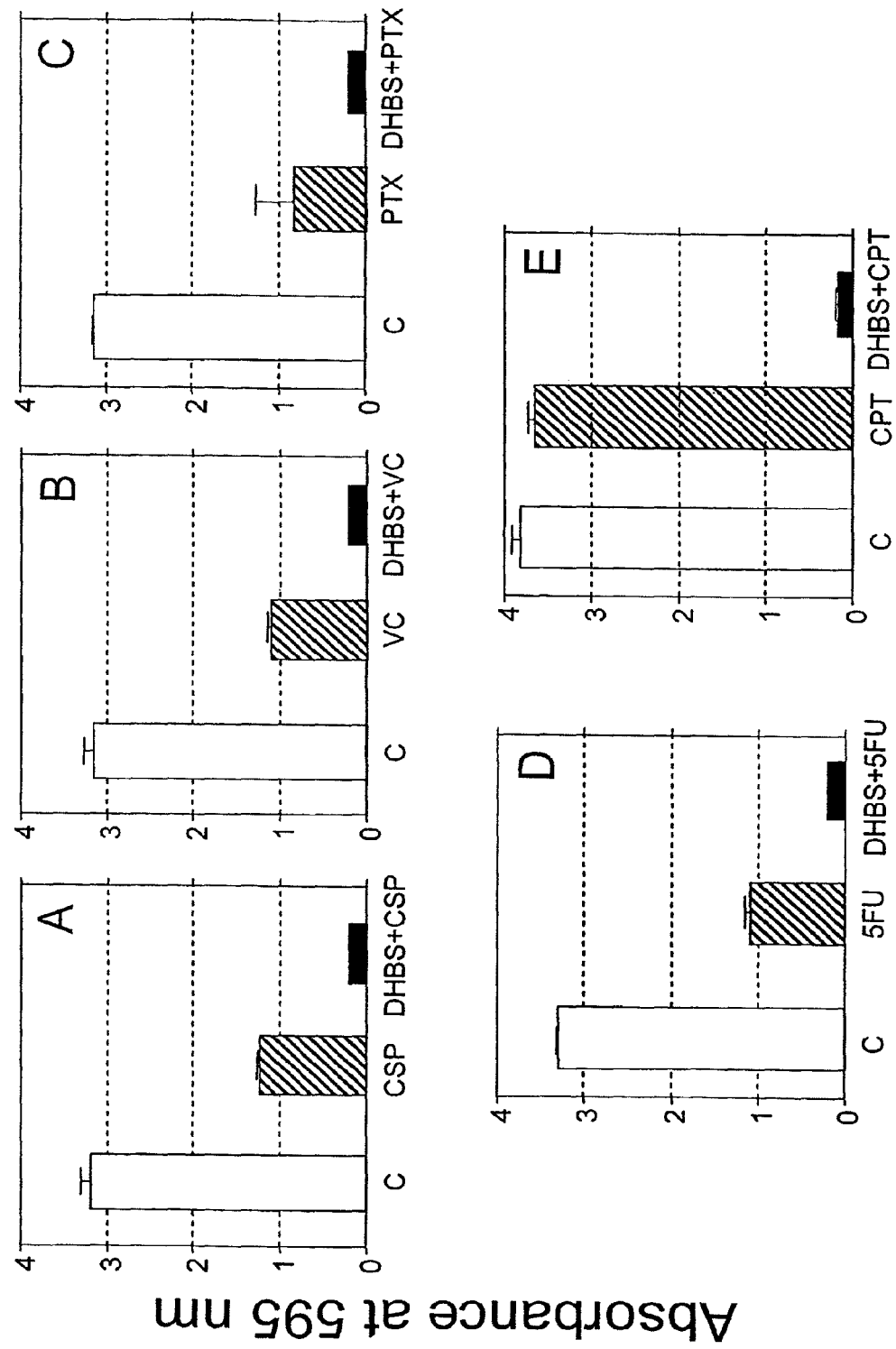
FIG. 2 shows the effect of the treatment with 2,5-dihydroxybenzene sulfonate (DHBS; 100 µM) on the proliferation of C6 rat glioma cells for the cytostatic agents, cisplatin (CSP; 5 µg/ml) (Panel A), vincristine (VC; 0.5 µg/ml) (Panel B), paclitaxel (PTX; 5 µg/ml) (Panel C), 5-fluorouracil (5FU; 100 µg/ml) (Panel D) and irinotecan (CPT; 0.1 µg/ml) (Panel E). DHBS was either administered or not administered after seeding the C6 cells ($10^4$ per well) until fixation of the cells at 96 h. The cells were treated with the cytostatic agents for the last 48 h. The y axes gives the absorbance at 595 nm. Data are expressed as mean±SEM of the absorbance at 595 nm that is proportional to the number of cells stained with crystal violet from 3 experiments for each cytostatic agent. Open bars represent control cells; stripped bars represent cells treated with the respective cytostatic agent and solid bars represent cells treated with the combination of DHBS and each one of the cytostatic agent. In all cases, $p<0.001$ group treated with cytostatic agent alone vs group treated with DHBS plus the cytostatic agent.

As shown in FIG. 2 all the cystostatic agents used, except for irinotecan, partially inhibited C6 glioma cell proliferation. However, a markedly enhanced inhibition of proliferation of glioma cells was observed in all cases when the cells were pre-treated with 2,5-dihydroxybenzene sulfonate. Thus, 2,5-dihydroxybenzene sulfonate enhances the sensitivity of glioma cells to the anti-proliferative action of the cytostatic agents.

Example 3

Figure 3:
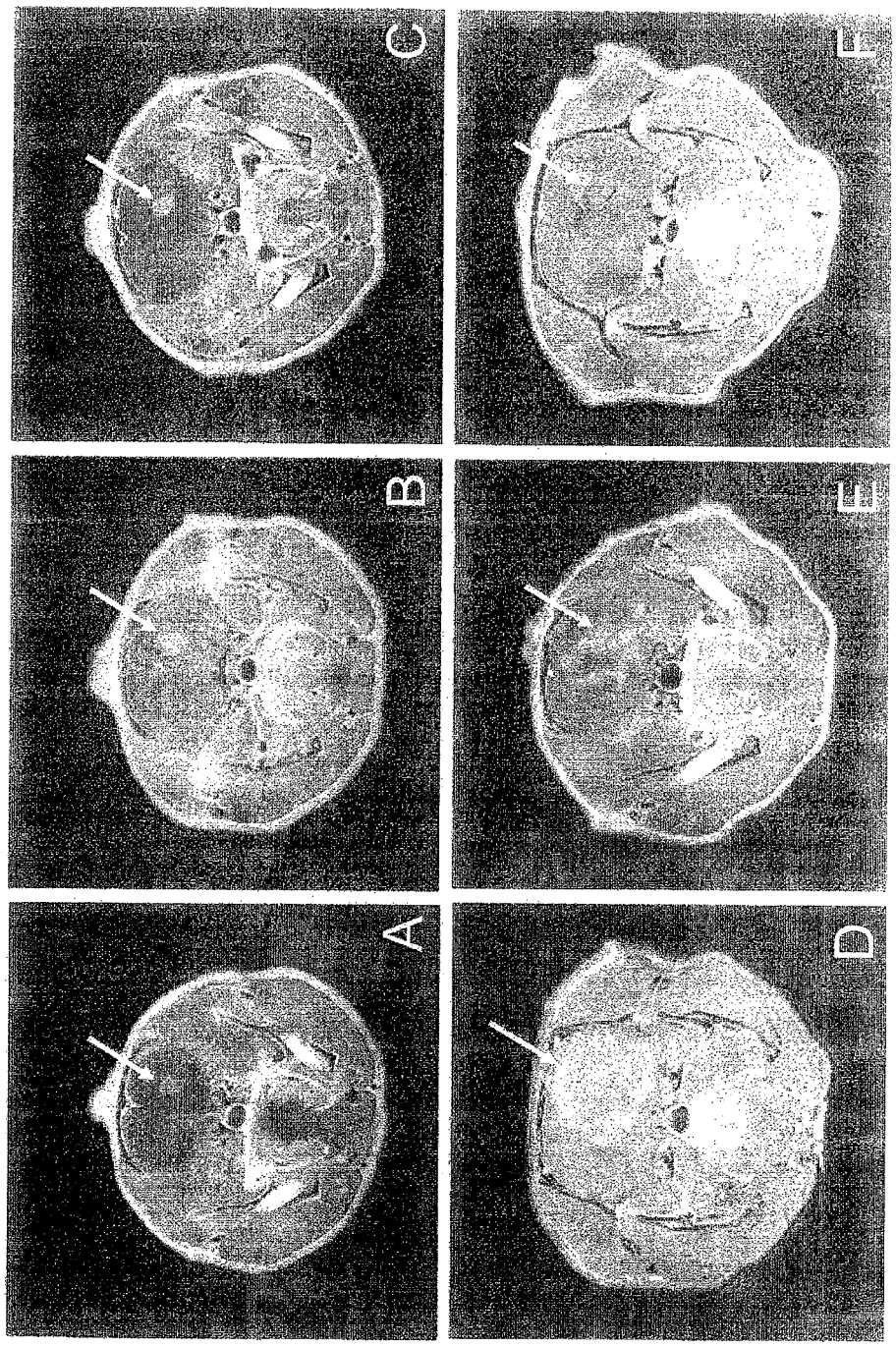
FIG. 3 upper panels A, B and C, are the magnetic resonance images (MRIs) of rat brains showing the presence of tumours (indicated by the arrows) two weeks after the implantation of $10^6$ glioma cells. MRIs were obtained before the treatment with irinotecan in two four-days cycles separated by a four-days resting period (Panel A), before the treatment with 2,5-dihydroxybenzene sulfonate (DHBS) (Panel B) or before the treatment with the combination of irinotecan plus 2,5-dihydroxybenzene sulfonate (Panel C). The lower panels D, E and F are the MRIs from rat brains showing the progression of the tumours (indicated by arrows) 6 weeks after the implantation of C6 glioma cells. Panel D shows the MRIs after treatment with irinotecan (CPT-11; 10 mg/kg/day; i.p.); Panel E shows the MRIs after treatment with 2,5-dihydroxybenzene sulfonate (200 mg/kg/day; i.p.); (Panel F shows the MRIs after treatment with the combination of irinotecan (CPT-11; 10 mg/kg/day; i.p.) plus 2,5-dihydroxybenzene sulfonate (200 mg/kg/day; i.p.). Treatments were started 4 weeks after implantation.

2,5-Dihydroxybenzene Sulfonate Increases the Efficacy of Irinotecan (CPT-11) in Rat Glioma Cultures of rat glioma C6 cells were grown as described in Cuevas P et al. *Neurol. Res.*, 27: 797-800 (2005). Confluent C6 cells cultured in 75 cm² flasks were detached and implanted into the left frontal lobe of anaesthetized rats using a stereotactic device. The implantation of the $10^6$ glioma cells was accomplished by means of a Hamilton syringe coupled to a glass pipette (40-60 μm in diameter) through a small orifice performed in the ceranium by a stainless steel needle. FIG. 3, panels A, B and C shows the magnetic resonance image of the rat brain two weeks after implantation. Ten days after the existence of a tumour was confirmed, rats were randomly assigned to receive or not receive 2,5-dihydroxybenzene sulfonate (200 mg/kg/day in saline; i.p) throughout the period of observation. Two days after starting the treatment with 2,5-dihydroxybenzene sulfonate, the rats were treated with irinotecan (CPT-11; 10 mg/kg/day; i.p. Campto® solution (20 mg/ml; Aventis, Madrid, Spain) or saline in two four-days cycles separated by a four-days resting period. After the treatment (6 weeks after implantation of glioma cells), FIG. 2, panels D, E and F show the magnetic resonance images of the brain obtained from rats treated with irinotecan, 2,5-dihydroxybenzene sulfonate or the combination of irinotecan and 2,5-dihydroxybenzene sulfonate respectively, n=3 rats (irinotecan); n=4 rats (DHBS); n=4 rats (irinotecan+DHBS)

As can be seen in FIG. 3, panel D, six weeks after the implantation of glioma cells, the rats treated only with irinotecan had a large sized brain tumour, surpassing the size of the rat cerebral hemisphere. Rats treated only with 2,5-dihydroxybenzene sulfonate presented a brain tumour smaller than that observed in the irinotecan-treated rat, and with altered distribution of the contrast agent (FIG. 3, panel E). The rat treated with 2,5-dihydroxybenzene sulfonate plus irinotecan had a smaller sized brain tumour than that observed in the other two treatments, with poor distribution of the contrast agent (FIG. 3, panel F). Thus, the treatment with 2,5-dihydroxybenzene sulfonate increases the efficacy of the cytostatic agent, irinotecan, to reduce the progression of an established orthotropic glioma.

Example 4

Effect of 2,5-Dihydroxybenzene Sulfonate on the Progression of Established Rat Subcutaneous Gliomas Confluent C6 cells cultured as described in Example 2 were detached and subcutaneously implanted under the dorsal skin in anaesthetized rats. One week after the implantation of the tumour cells, the rats were randomly assigned to receive intra-tumoural injection of 2,5-dihydroxybenzene sulfonate (100 mg/kg in saline) or saline twice a day. Ten days after starting the treatment, subcutaneous heterotopic gliomas were removed from the rats and their volumes were calculated.

Figure 4:
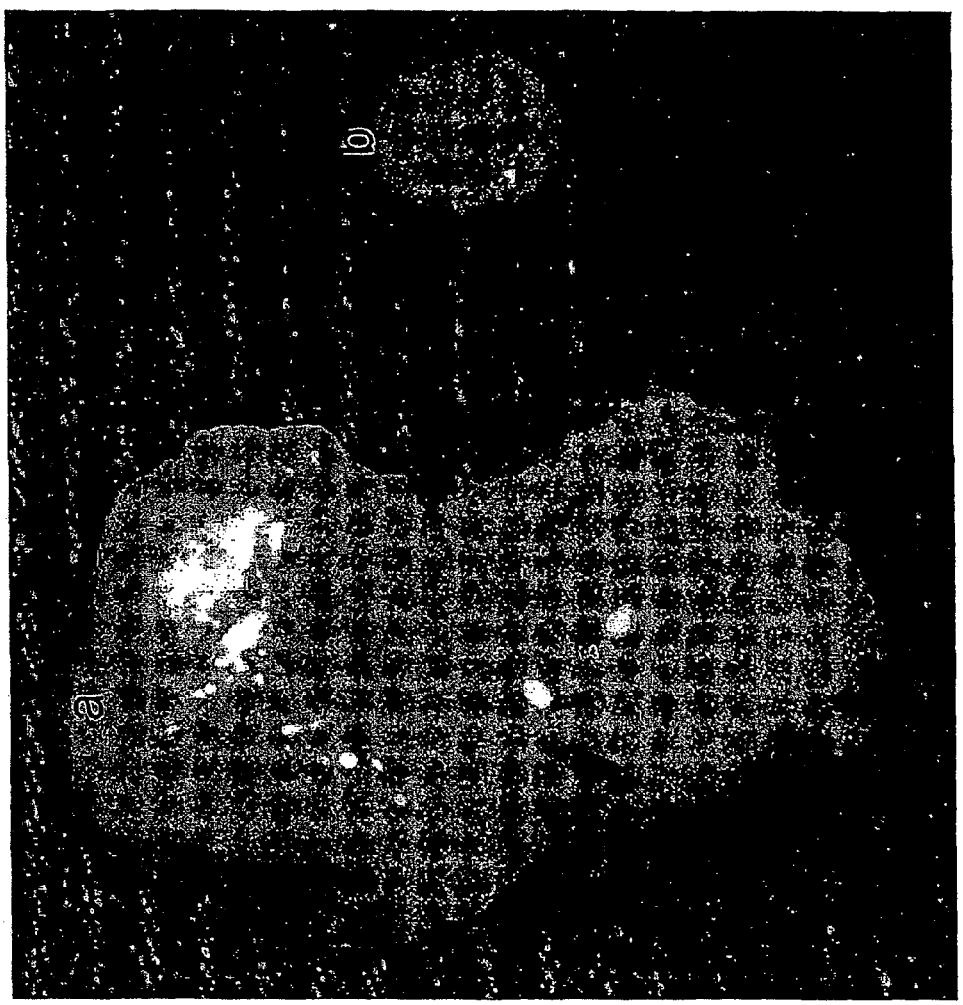
FIG. 4 is a photograph showing the difference in size between two heterotopic gliomas developed after subcutaneous implantation of $5\times10^5$ C6 glioma cells in a saline-treated rat (a) and in a rat treated with intra-tumoural injection of 2,5-dihydroxybenzene sulfonate (100 mg/kg) (b). Turnovers were removed 10 days after treatment, which was done one week after implantation of tumour cells.
Figure 5:
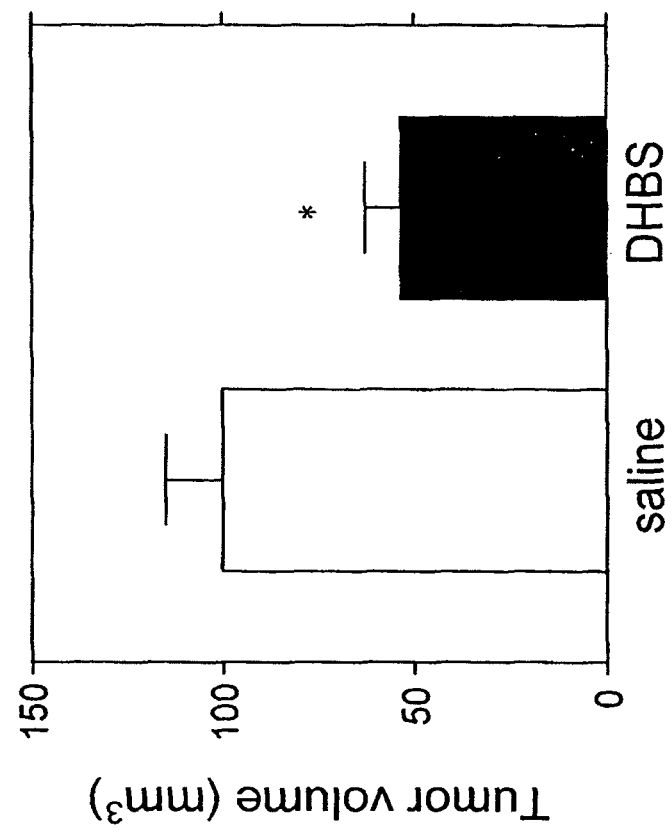
FIG. 5 shows the effects of intraperitoneal administration of 2,5-dihydroxybenzene sulfonate (DHBS; 100 mg/kg/twice a day for 10 days) or saline on the progression of established rat subcutaneous gliomas. Data are expressed as mean±SEM of tumor volume in $mm^3$ from 6 rats per group, *$p<0.05$ vs saline by unpaired t-test.

FIG. 4 shows that the tumour obtained collected from saline-treated rats (a) was markedly larger than the tumours obtained from rats treated by intra-tumoural injection of 2,5-dihydroxybenzene sulfonate (b). FIG. 5 shows that the volume of tumours from rats intraperitoneally treated with 2,5-dihydroxybenzene sulfonate was significantly reduced when compared to saline-treated rats thereby demonstrating the inhibitory effect of 2,5-dihydroxybenzene sulfonate in the progression of established heterotopic gliomas.

Example 5

Effect of 2,5-Dihydroxybenzene Sulfonate on Melanoma Growth

Figure 6:
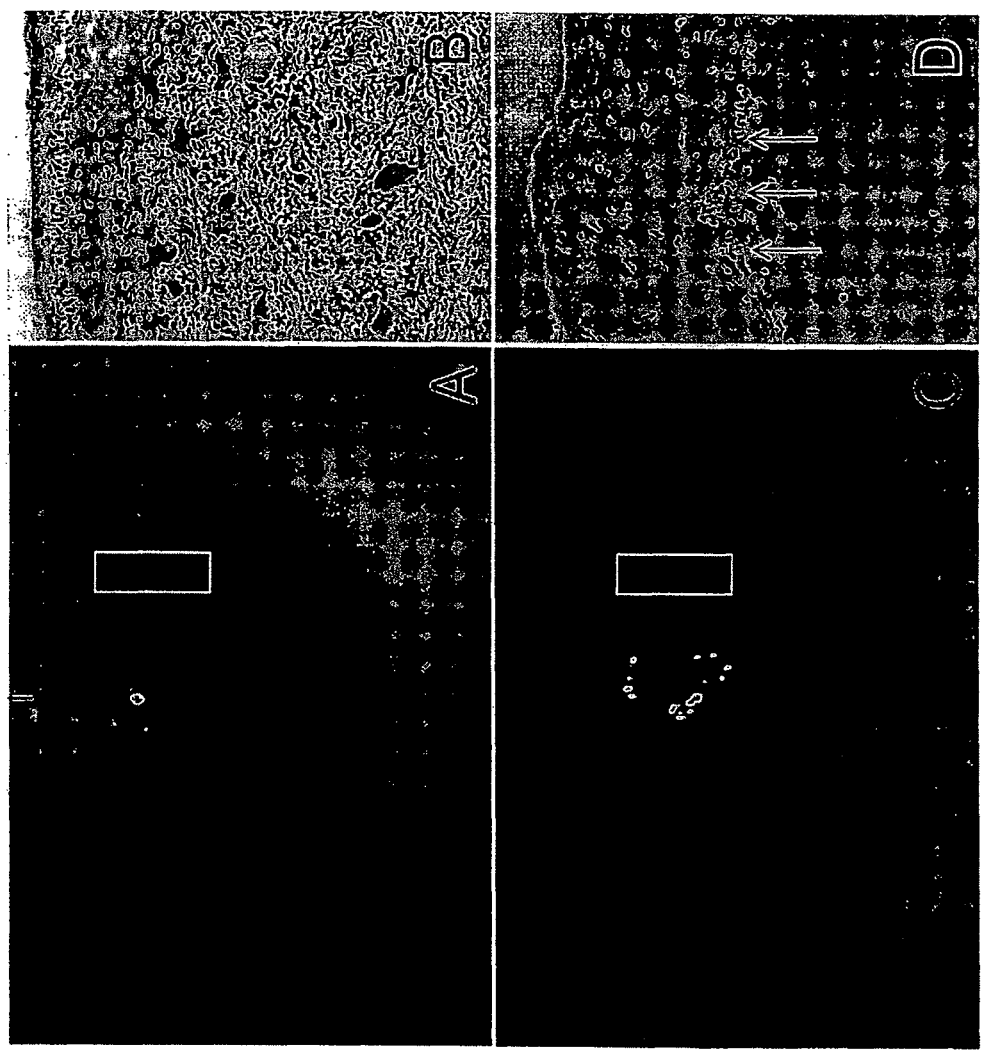
FIG. 6 are photographs showing the effects of 2,5-dihydroxybenzene sulfonate on melanoma growth. Panel A shows the melanoma in rabbit cornea in an untreated animal. Panel B depicts the histological feature of the melanoma obtained from the boxed area in Panel A. The strong tumor angiogenesis are indicated by asterisks in Panel B. Panel C shows the reduced melanoma growth in an animal treated with 2,5-dihydroxybenzene sulfonate (200 mg/ml; 0.5 ml/h for 14 days). Panel C depicts the histological feature from the boxed area in panel C. Scarce tumor cells (marked by arrows) and absence of angiogenesis was observed.

New Zealand White Rabbits (weight 3.0±0.5 kg) were used. All surgical procedures were performed under intra-muscular general anaesthesia (xylazine hydrochloride, 5 mg/kg). The rabbit eyes were treated with licalin, an ophthalmic solution for surface anaesthesia. Using a surgical microscope a millimetre fragment of human melanoma biopsy was implanted into a pocket made in the stroma of the cornea. About 2 mm away from the limbal origin of the cornea. An osmotic minipump (Alzet 2002, Alza Corporation, Palo Alto, Calif., USA) was implanted subcutaneously into the rabbit neck region to ensure continuous infusion of either saline or 2,5-dihydroxybenzene sulfonate (200 mg/ml in saline). A delivery catheter was placed free in the solera through a tunnel performed into the superior tharsus to deliver either 2,5-dihydroxybenzene sulfonate or saline at a constant rate of 0.5 μl/h. To ensure a constant ocular concentration of 2,5-dihydroxybenzene sulfonate a tharsoraphy was performed. After 14 days of therapy, corneas were removed and processed for histological examination (10% formalin fixation, alcohol dehydration and paraffin embedding). FIG. 6 shows that the melanoma in rats treated with 2,5-dihydroxybenzene sulfonate (panels C and D) was reduced relative to rabbits treated with saline (panels A and B).

Example 6

Figure 7:
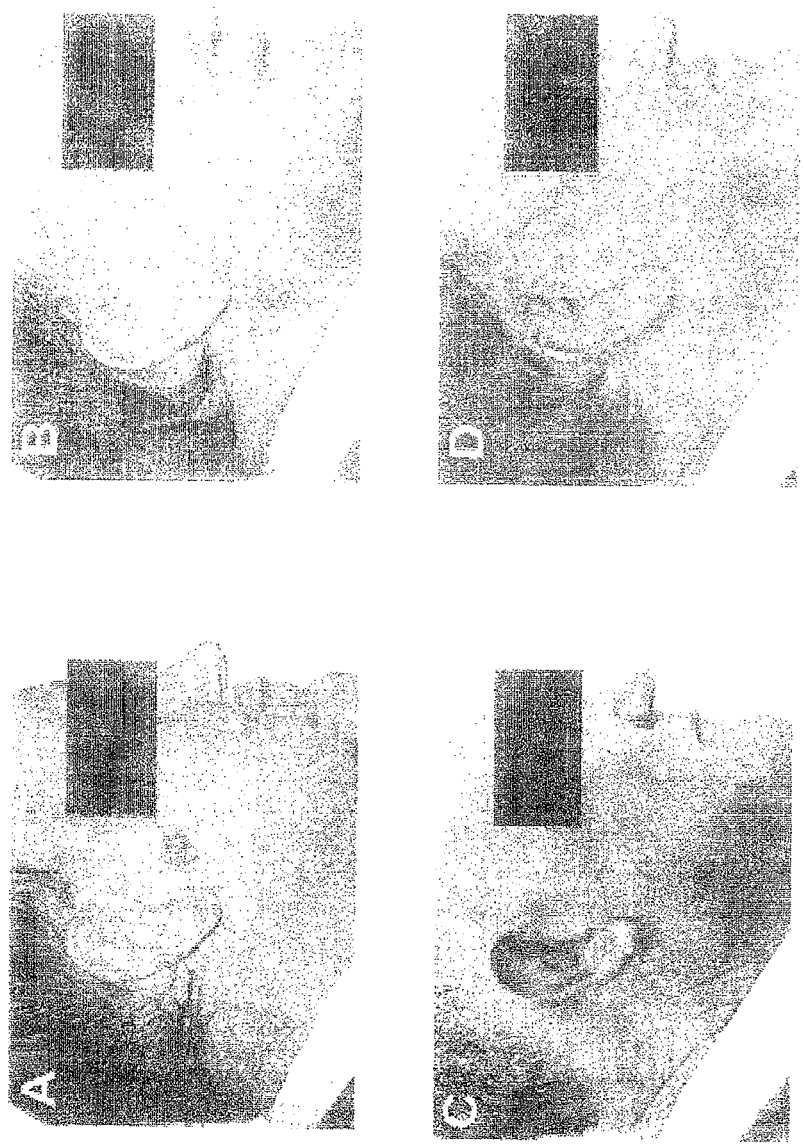
FIG. 7 shows photographs of a patient with infiltrative BCC; Panel A before treatment; Panels B and C at 2 and 4 weeks, respectively, after topical treatment with 2,5-dihydroxybenzene sulfonate cream (2.5%) twice a day; Panel D shows the patient 6 weeks after finishing treatment.
Figure 8:
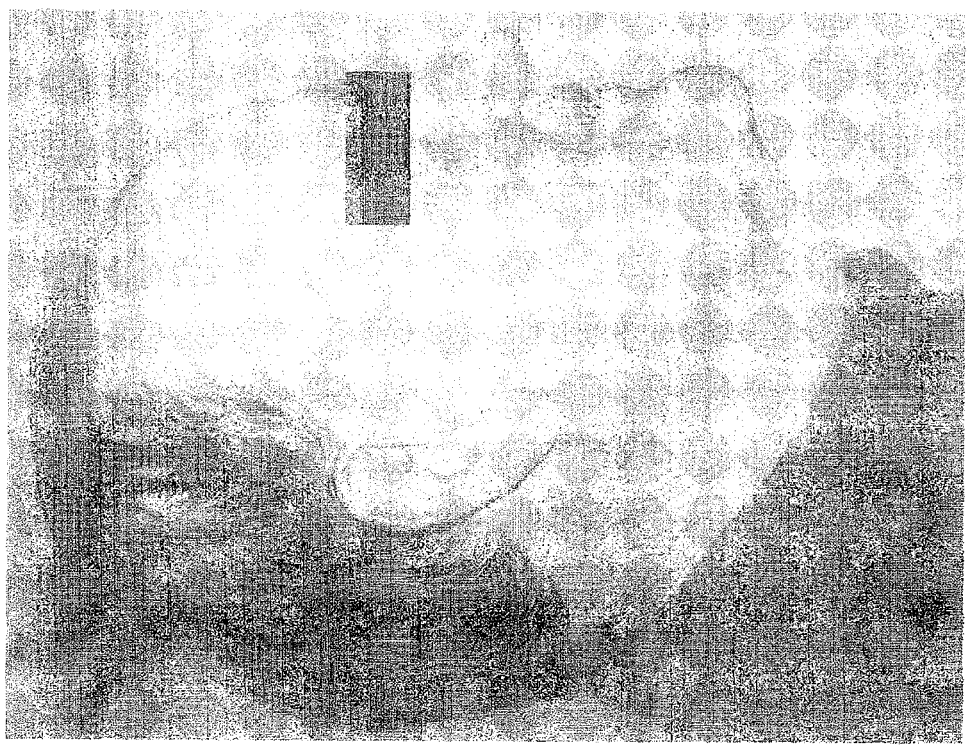
FIG. 8 shows the photograph of the same patient as in FIG. 7 two years after completion of the treatment with 2,5-dihydroxybenzene sulfonate cream (2.5%).
Figure 9:
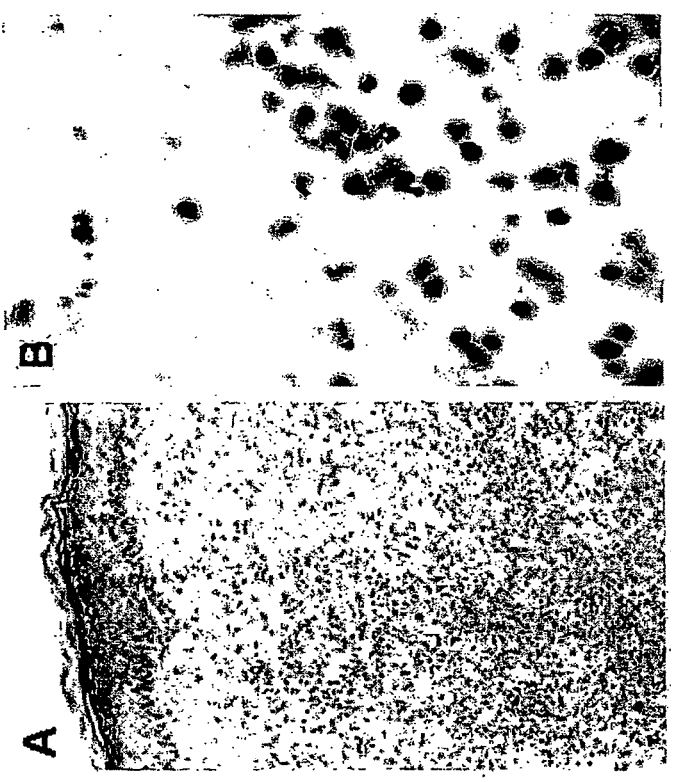
FIG. 9 shows the histopathological pictures after 4 weeks of treatment with 2,5-dihydroxybenzene sulfonate cream (2.5%). Panel A shows there is no evidence of BCC in section specimen (Masson's trichrome staining; original magnification×22). Panel B is the same specimen as shown in Panel A), shows the presence of apoptotic cells that were revealed by the terminal 2'-deoxyuridine-5'-triphosphate (dUTP) nick-end-labelling (TUNEL) positive cells with brown nuclei (stained by the TUNEL technique; original magnification×65).
Figure 10:
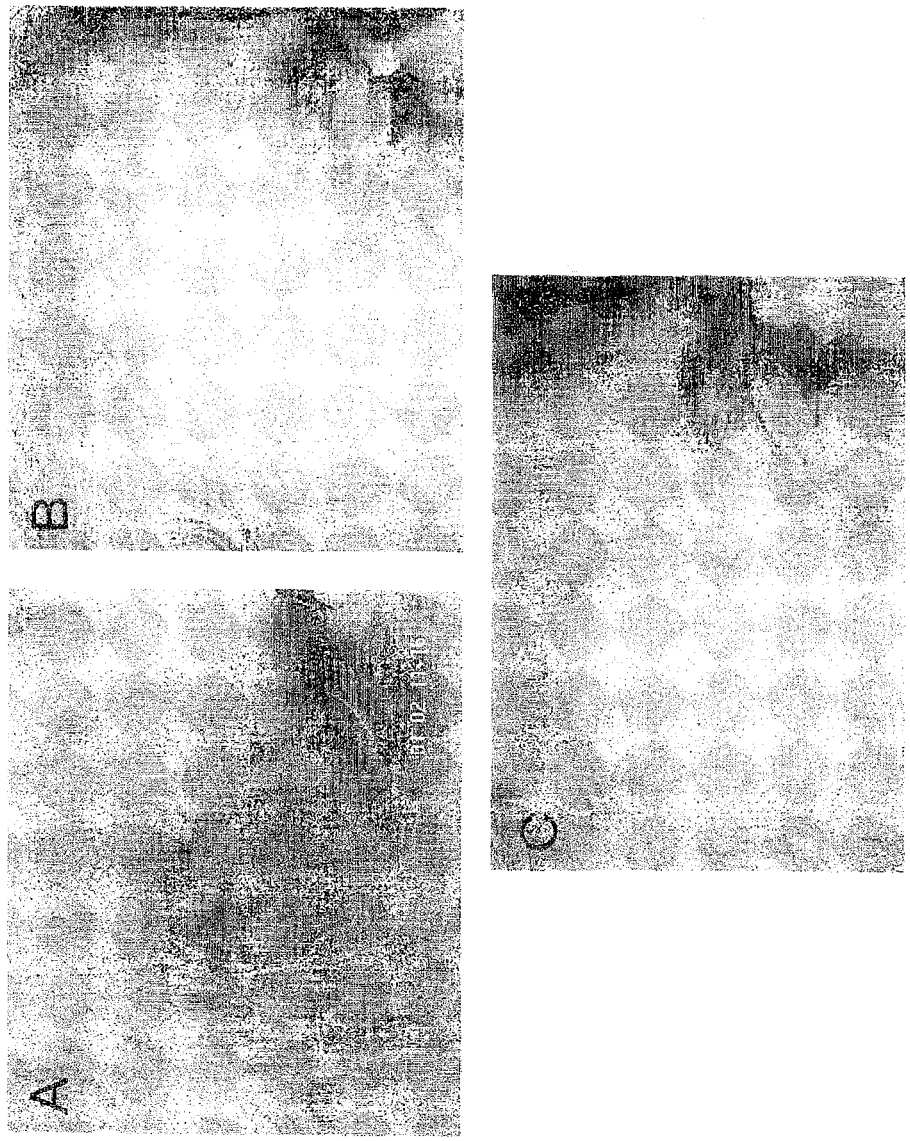
FIG. 10 shows photographs of a patient with infiltrative BCC: Panel A before treatment; Panel B after two months of topical treatment with 2,5-dihydroxybenzene sulfonate cream (2.5%) twice a day; Panel C six months after completion of the topical treatment with 2,5-dihydroxybenzene sulfonate cream (2.5%) twice a day.
Figure 11:
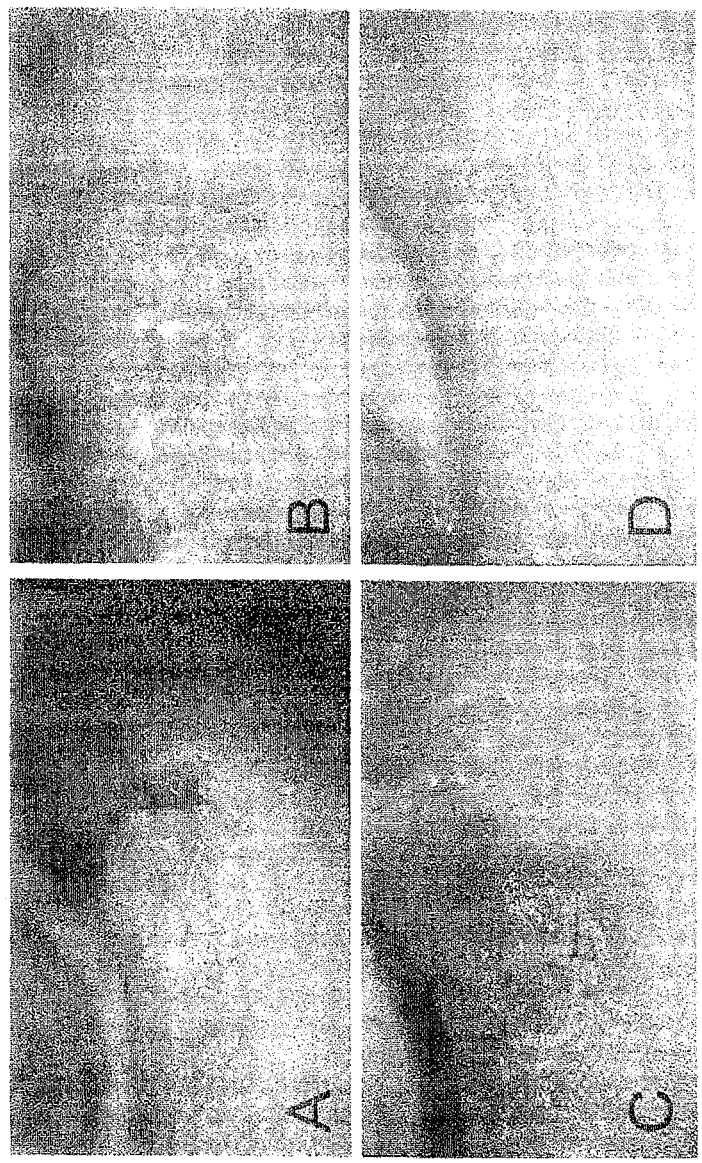
FIG. 11 shows photographs of a patient with nodular BCC: Panel A before treatment; Panel B after two months of topical treatment with 2,5-dihydroxybenzene sulfonate cream (2.5%) twice a day; Panels B and C two different times during the topical treatment with 2,5-dihydroxybenzene sulfonate cream (2.5%) twice a day; Panel D after six months of topical treatment with 2,5-dihydroxybenzene sulfonate cream (2.5%) twice a day.
Figure 12:
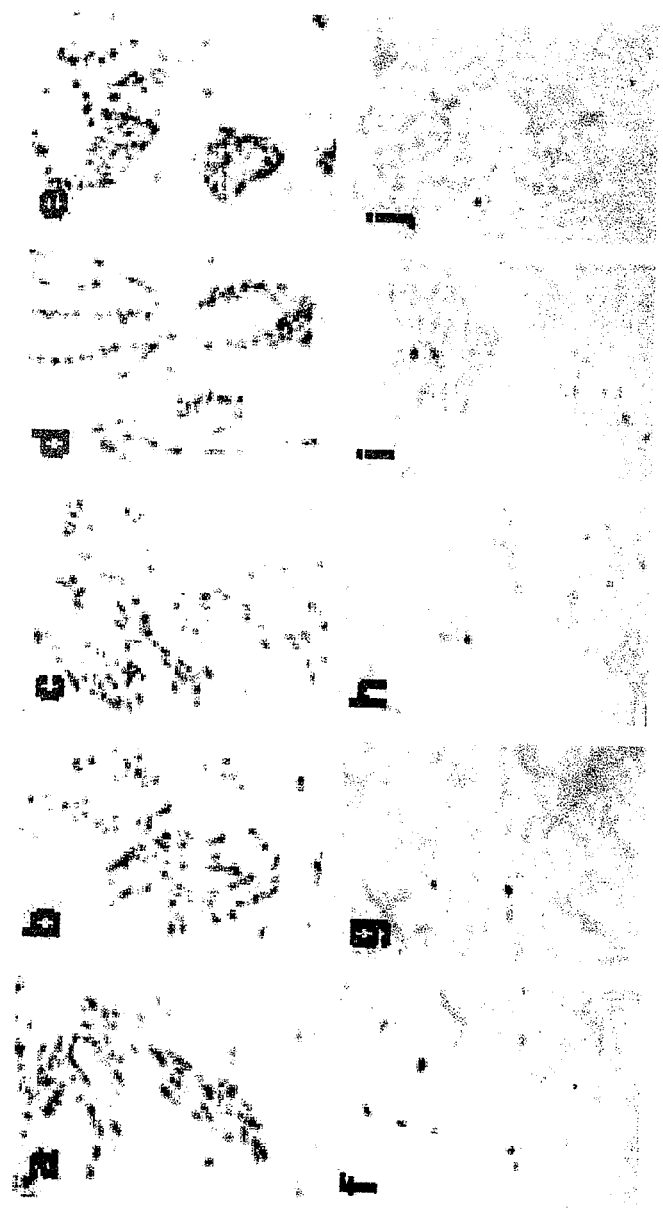
FIG. 12 shows the immunohistochemical detection of the cell proliferation rate in dermal tissue of skin specimens from 5 different patients with basal cell carcinoma before treatment (Panels a, b, c, d, e, respectively) and in specimens from the same patients after topical treatment with 2,5-dihydroxybenzene sulfonate cream (2.5%) twice a day for two months (Panels f, g. h, i, j, respectively). Immunostaining with chromogen diaminobenzidine (DAB) revealed the presence of Ki-67, a marker for cell proliferation.
Figure 13:
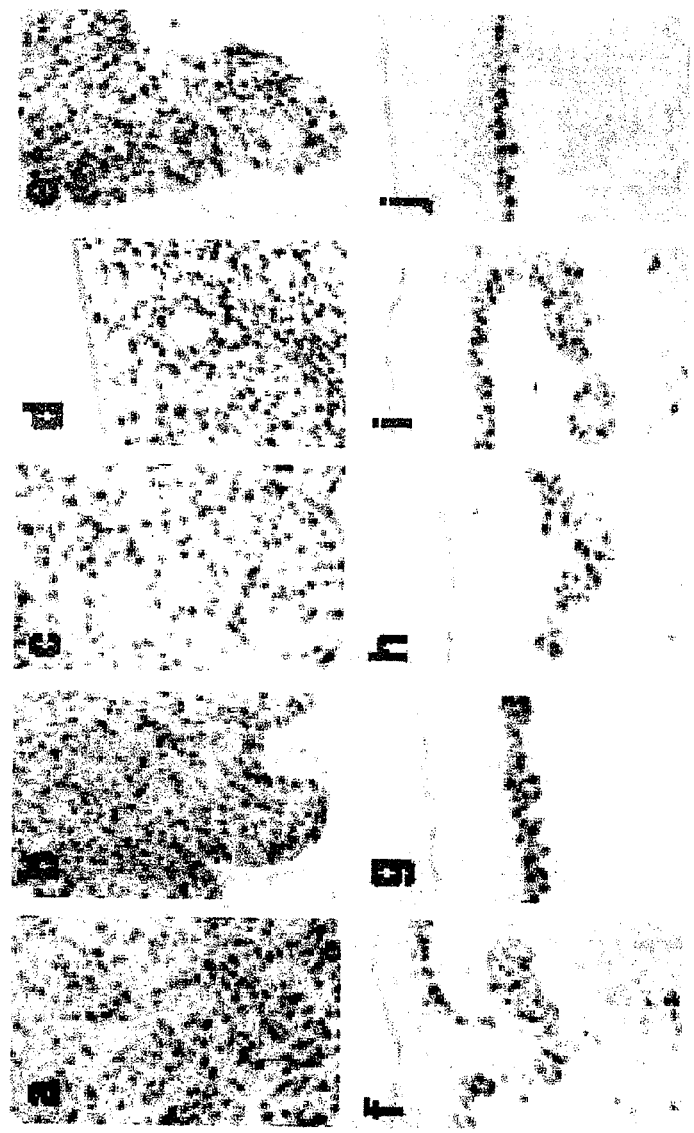
FIG. 13 shows the immunohistochemical detection of the cell proliferation rate in epidermal tissue of skin specimens from 5 different patients with basal cell carcinoma before treatment (Panels a, b, c, d, e, respectively) and in specimens from the same patients after topical treatment with 2,5-dihydroxybenzene sulfonate cream (2.5%) twice a day for two months (Panels f, g, h, i, j, respectively). Immunostaining with chromogen diaminobenzidine (DAB) revealed the presence of Ki-67, a marker for cell proliferation.
Figure 14:
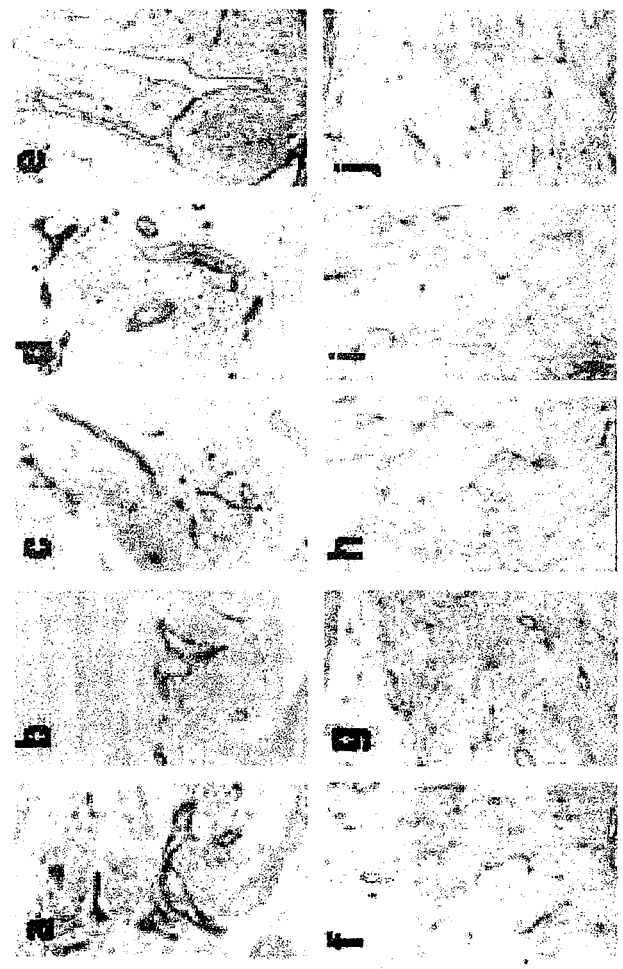
FIG. 14 shows the immunohistochemical detection of vascularization in dermal tissue of skin specimens from 5 different patients with basal cell carcinoma before treatment (Panels a, b, c, d, e, respectively) and in specimens from the same patients after topical treatment with 2,5-dihydroxybenzene sulfonate cream (2.5%) twice a day for two months (Panels f, g, h, i, j, respectively). Immunostaining with chromogen diaminobenzidine (DAB) revealed the presence of CD34, a marker for vascularization.
Figure 15:
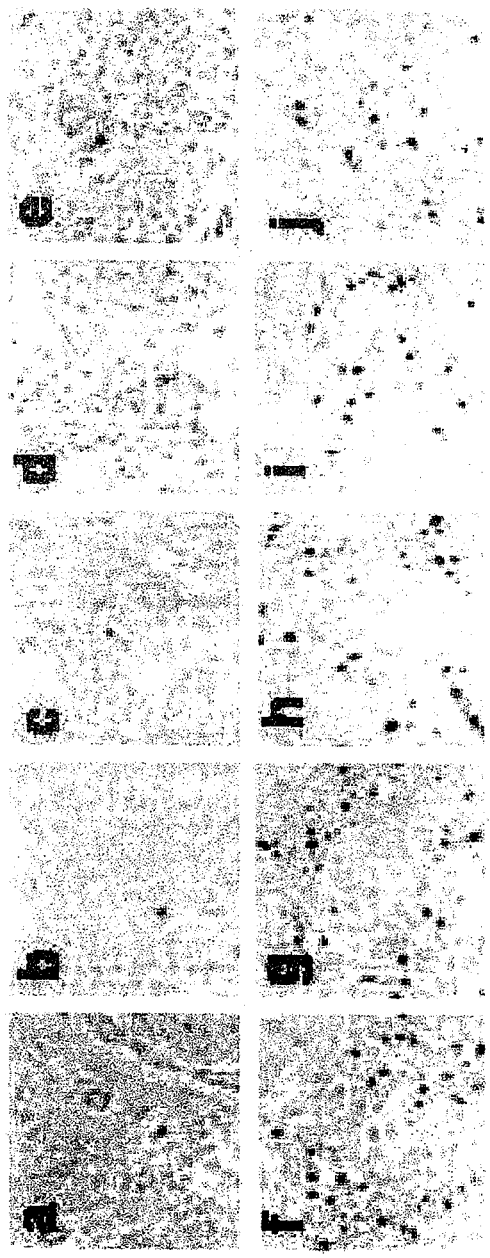
FIG. 15 shows the histological detection of apoptosis rate in dermal tissue of skin specimens from 5 different patients with basal cell carcinoma before treatment (Panels a, b, c, d, e, respectively) and in specimens from the same patients after topical treatment with 2,5-dihydroxybenzene sulfonate cream (2.5%) twice a day for two months (Panels f, g, h, i, j, respectively). The presence of apoptotic cells was revealed by the terminal 2'-deoxyuridine-5'-triphosphate (dUTP) nick-end-labelling (TUNEL) method.

Effect of 2,5-Dihydroxybenzene Sulfonate on Basal Cell Carcinoma 2,5-dihydroxybenzene sulfonate cream (2.5%) was applies topically twice a day to the lesions of a patient with basal cell carcinoma (BCC). As shown in FIG. 7, the lesion in the patient with facial infiltrative BCC were cleared after 4 weeks of treatment, with no recurrence for a two years period after treatment (FIG. 8). Treatment with 2,5-dihydroxybenzene sulfonate (2.5%), cleared the histopathological signs of BCC and increased the rate of apoptosis (FIG. 9). Topical administration of 2,5-dihydroxybenzene sulfonate cream (2.5%) twice a day for two months also cleared the lesion in two other patients with infiltrative BCC, showing no recurrence six months after treatment completion (FIG. 10). BCC tumour lesions of a nodular type from two additional patients disappeared after six months of treatment with topical administration of 2,5-dihydroxybenzene sulfonate cream (2.5%) twice a day (FIG. 11). Topical administration of 2,5-dihydroxybenzene sulfonate cream twice a day inhibited proliferation rate in dermis and epidermis in BCC specimens from 5 different patients (FIGS. 12 and 13). In addition, the treatment with 2,5-dihydroxybenzene sulfonate cream (2.5%) inhibited vascularization and increased apoptosis rate in these 5 patients (FIGS. 14 and 15).

Example 7

Effect of 2,5-Dihydroxybenzene Sulfonate on Rosacea

Figure 16:
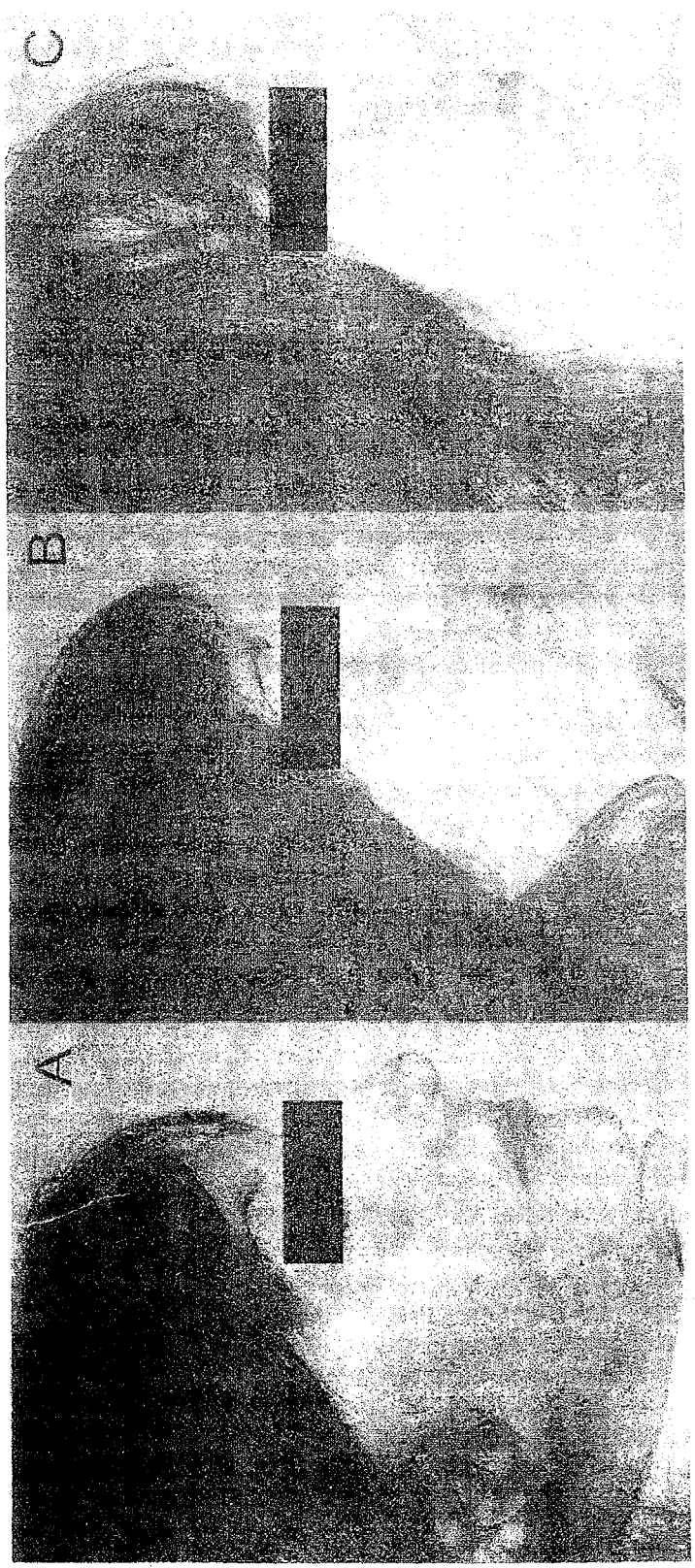
FIG. 16 shows the photograph of a patient with rosacea: Panel A before treatment; Panel B after two months of topical treatment with 2,5-dihydroxybenzene sulfonate cream (2.5%) twice a day; Panel C one year post-treatment (C).

A woman with facial rosacea was treated twice a day with 2,5-dihydroxybenzene sulfonate cream (2.5) by topical application in the affected area for two months. As shown in FIG. 16 topical treatment with 2,5-dihydroxybenzene sulfonate cream led to a significant improvement in erythema and telangectasia. Furthermore, the symptoms of flushing, burning and stinging sensations were all reduced after treatment, with no recurrence one year after stopping the treatment.

Example 8

Effect of 2,5-Dihydroxybenzene Sulfonate on Rosacea

Figure 17:
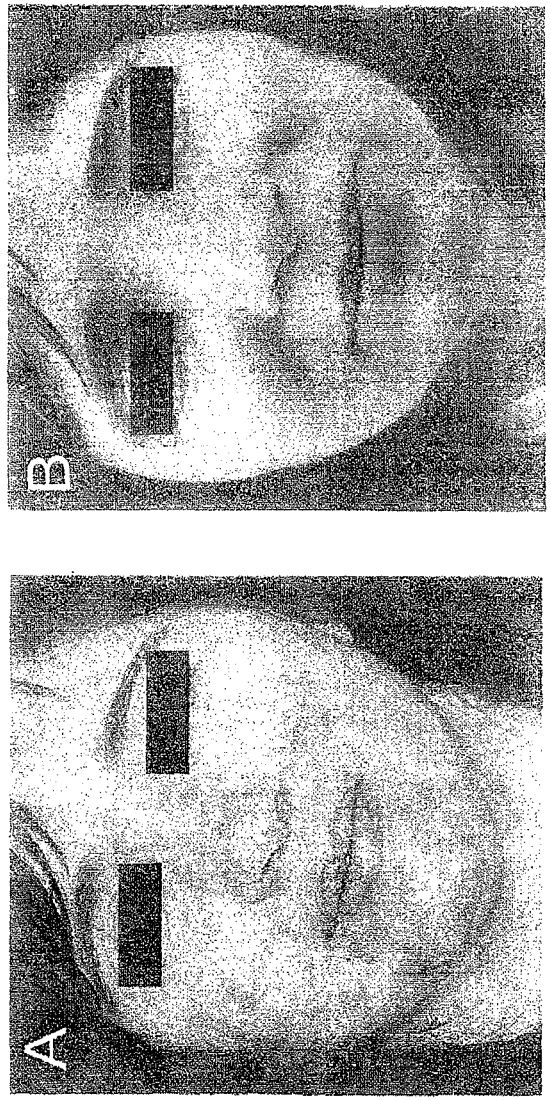
FIG. 17 shows the photograph of a patient with rosacea: Panel A before treatment; Panel B after three weeks of topical treatment with 2,5-dihydroxybenzene sulfonate cream (2.5%) twice a day.

A woman with facial rosacea was treated twice a day with 2,5-dihydroxybenzene sulfonate cream (2.5%) by topical application in the affected area for three weeks. As shown in FIG. 17 topical treatment with 2,5-dihydroxybenzene sulfonate cream led to a significant improvement in erythema and telangectasia.

Example 9

Effect of 2,5-Dihydroxybenzene Sulfonate on Psoriatic Lesions

The potassium salt of 2,5-dihydroxybenzene sulfonic acid was formulated at 2.5 and 5% as a cream that is typically used for the topical treatment of skin diseases. The selected concentrations of the 2,5-dihydroxybenzene sulfonic acid salt is within the range of the concentrations used for treatment of diabetic retinopathies; 6 tablets per day of 500 mg of calcium salt of the 2,5-dihydroxybenzene sulfonic acid (Benakis A et al Thérapie 1974; 29: 211-219). Distilled water was used as the aqueous phase of the cream. The fatty phase was by cetylic alcohol, stearic alcohol or Vaseline. The span is an emulsifier efficient in the preparation of the cream. Although both formulations (2,5 and 5%) of the product was shown to be clinically efficient, the best therapeutic benefit was obtained at the concentration of 5%. Hence the results herein are those obtained with the 2,5-dihydroxybenzene sulfonic acid formulated in the cream at 5%.

The following example illustrates one formulation of an efficient cream for the topic treatment of psoriasis:

Active Component: (potassium salt of the 2,5-dihydroxybenzene sulfonic acid at 5.6%)

Inactive Component: cetylic alcohol (2.5%), stearyl alcohol (2.5%), liquid Vaseline (30%), white soft paraffin (20%), sorbinate dcato (5%) and distilled water (c.s.p. 100 g).

Figure 18:
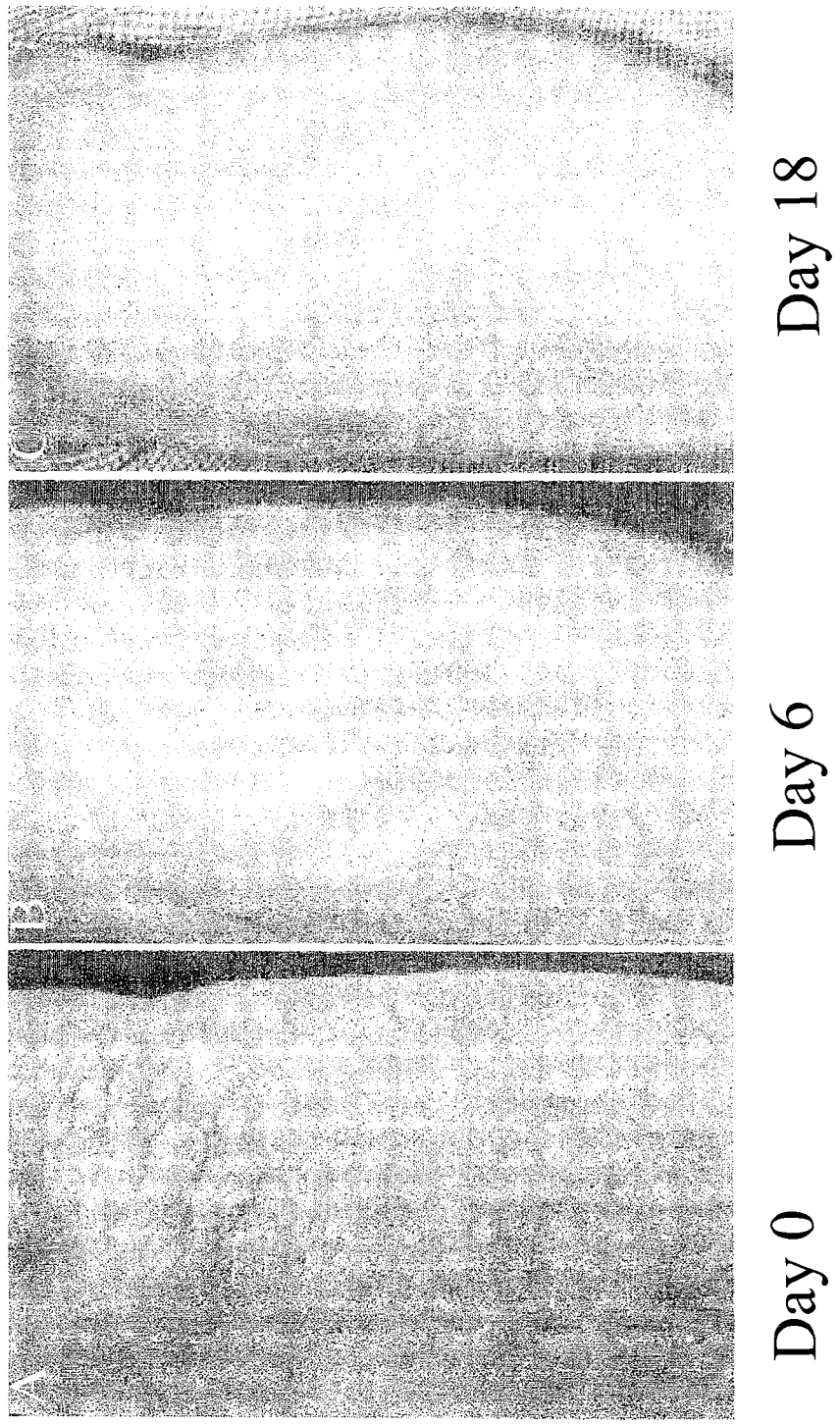
FIG. 18 shows the images of a hiperkeratosic psoriatic plaque located in the rear region of the left elbow of a patient. Image A shows the psoriatic plaque before treatment (day 0). Image B is the same plaque after six days of treatment with a cream that contains 5% of the potassium salt of the 2,5-dihydroxybenzene sulfonic acid. Image C shows the psoriatic plaque after 18 days of treatment with a cream that contains 5% of the potassium salt of the 2,5-dihydroxybenzene sulfonic acid.

The clinical efficacy of the treatment was evaluated in accordance with the index that quantifies the desquamation signs (D), erythema (E) and infiltration (I) to which the following scoring system was assigned: (0) absent; (1) slight; (2) moderate and (3) severe (Freeman A. K. et al. J Am. Acad Dermat 2003; 48: 564-568). FIG. 18 shows the images before treatment, six and eighteen days after treatment of the same chronic psoriatic plaque located at the extension of the left elbow treated with the potassium salt of the 2,5-dihydroxybenzene sulfonic acid at 5%. As was observed, the topical treatment two times a day with a cream containing the potassium salt of the 2,5-dihydroxybenzene sulfonic acid produces an early (6 days) very notable "clearing" of the plaque with almost total disappearance of hyperkeratosis. The therapeutic efficacy of the cream is more evident at the end of the second week of treatment (18 days).

The treatment produces a significant reduction of the global values of the DEI index (DEI global pre-treatment=6±1.57 vs. DEI global post-treatment=10.58; p<0.0001; unpaired student's t test).

The disclosure of each patent, patent application and publication cited or described in the present specification is hereby incorporated by reference herein in its entirety.

Although the invention has been set forth in detail, one skilled in the art will appreciate that numerous changes and modifications can be made to the invention, and that such changes and modifications can be made without departing from the spirit and scope of the invention.

What is claimed is:

1. A method of treating skin cancer comprising administering topically to said patient a therapeutically effective amount of a compound of Formula (I) or a pharmaceutically acceptable salt thereof:
   wherein the compound of Formula (I) is:

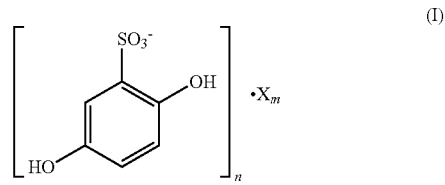

(I)

wherein:
   X is hydrogen, an organic cation or an inorganic cation;
   n is an integer from 1 to 2; and
   m is an integer from 1 to 2.

2. The method of claim 1, wherein the compound of Formula (I) is present in a composition together with a pharmaceutically acceptable excipient.

3. The method of claim 1, wherein the compound of Formula (I) is selected from the group consisting of:
   2,5-dihydroxybenzene sulfonic acid;
   calcium 2,5-dihydroxybenzenesulfonate;
   sodium 2,5-dihydroxybenzenesulfonate;
   magnesium 2,5-dihydroxybenzenesulfonate;
   lithium 2,5-dihydroxybenzenesulfonate; and
   diethylamine 2,5-dihydroxybenzenesulfonate.

4. The method of claim 1, further comprising administering at least one therapeutic agent.

5. The method of claim 4, wherein the therapeutic agent is a chemotherapeutic agent, a steroid, a retinoid, an antimicrobial compound, an antioxidant, an anti-inflammatory compound, a NMDA receptor antagonist, an endothelin antagonist, an immunomodulating agent, a vitamin D analogue, salicylic acid, or a combination of two or more thereof.

6. The method of claim 1, wherein the administration is selected from topical, oral, buccal, parental, inhalation, or rectal.

* * * * *